United States Patent
Hoos et al.

(10) Patent No.: US 10,010,608 B2
(45) Date of Patent: Jul. 3, 2018

(54) COMBINATION THERAPIES FOR CANCER

(71) Applicants: MERCK SHARP & DOHME CORP., Rahway, NJ (US); NOVARTIS AG, Basel (CH)

(72) Inventors: Axel Hoos, Philadelphia, PA (US); Keith W. Orford, Philadelphia, PA (US); Patrick Chun, Kenilworth, NJ (US); Venkataraman Sriram, Palo Alto, CA (US); Elaine M. Pinheiro, Boston, MA (US); Scot W. Ebbinghaus, North Wales, PA (US)

(73) Assignees: MERCK SHARP & DOHME CORP., Rahway, NJ (US); NOVARTIS AG, Basel (CH)

(*) Notice: Subject to any disclaimer, the term of this patent is extended or adjusted under 35 U.S.C. 154(b) by 0 days.

(21) Appl. No.: 14/893,746

(22) PCT Filed: May 28, 2014

(86) PCT No.: PCT/US2014/039686
§ 371 (c)(1),
(2) Date: Nov. 24, 2015

(87) PCT Pub. No.: WO2014/193898
PCT Pub. Date: Dec. 4, 2014

(65) Prior Publication Data
US 2016/0106835 A1    Apr. 21, 2016

Related U.S. Application Data

(60) Provisional application No. 61/829,472, filed on May 31, 2013, provisional application No. 61/873,476, filed on Sep. 4, 2013, provisional application No. 61/981,906, filed on Apr. 21, 2014.

(51) Int. Cl.
| | | |
|---|---|---|
| *A61K 39/395* | (2006.01) | |
| *A61K 31/506* | (2006.01) | |
| *A61K 31/519* | (2006.01) | |
| *C07K 16/28* | (2006.01) | |
| *A61K 39/00* | (2006.01) | |

(52) U.S. Cl.
CPC ........ *A61K 39/3955* (2013.01); *A61K 31/506* (2013.01); *A61K 31/519* (2013.01); *C07K 16/2818* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 2012/0196879 A1 | 8/2012 | Dumble et al. | |
| 2014/0147411 A1* | 5/2014 | Pollack | A61K 38/212 424/85.2 |
| 2014/0248211 A1* | 9/2014 | Bender | A61K 45/06 424/1.49 |
| 2014/0341902 A1* | 11/2014 | Maecker | A61K 39/39558 424/135.1 |
| 2015/0023915 A1* | 1/2015 | Morrison | A61K 31/7048 424/85.4 |
| 2015/0210769 A1* | 7/2015 | Freeman | A61K 39/3955 424/136.1 |
| 2016/0257752 A1* | 9/2016 | Kim | C07K 16/2803 |

FOREIGN PATENT DOCUMENTS

| | | | |
|---|---|---|---|
| WO | 2006/121168 | * | 11/2006 |
| WO | 2008/156712 | * | 12/2008 |
| WO | 2009/114335 | * | 9/2009 |
| WO | 2011/047238 | * | 4/2011 |
| WO | 2013/019906 | * | 2/2013 |
| WO | 2013/019906 A1 | | 2/2013 |

OTHER PUBLICATIONS

Liu et al, Cancer Research, Proceedings: AACR Annual Meeting 2014, Apr. 5-9, 2014, abstract 5031.*
Flaherty et al New England Journal of Medicine vol. 367 p. 1697 (Nov. 1, 2012).*
Klinac et al. (Mar. 19, 2013) "Advances in personalized targeted treatment of metastatic melanoma and non-invasive tumor monitoring," Front. Oncol. 3:54. pp. 1-16.
International Preliminary Report on Patentability corresponding to International Patent Application No. PCT/US2014/039686, dated Dec. 1, 2015.
International Search Report corresponding to International Patent Application No. PCT/US2014/039686, dated Sep. 25, 2014.
American Association for Cancer Research (Jan. 30, 2014) "Combination Therapy Approved for Melanoma," Cancer Discovery. 4(3):262.
Burki (Jun. 2013) "Lambrolizumab induces advanced melanoma regression," Lancet Oncology. 14(8):297.
Domling et al. (Feb. 24, 2014) "Programmed death-1: therapeutic success after more than 100 years of cancer immunotherapy," Angewandte Chemie. 53(9):2286-2288.
Hamid et al. (Jul. 11, 2013) "Safety and Tumor Responses with Lambrolizumab (Anti-PD-1) in Melanoma," New England Journal of Medicine. 369(2):134-144.
Menzies et al. (Apr. 2014) "Dabrafenib and Trametinib, Alone and in Combination for BRAF-Mutant Metastatic Melanoma," Clinical Cancer Research. 20(8):2035-2043.

* cited by examiner

*Primary Examiner* — Sheela J Huff
(74) *Attorney, Agent, or Firm* — Lathrop Gage LLP; Brian C. Trinque

(57) ABSTRACT

A novel combination comprising a B-Raf inhibitor, particularly N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, the MEK inhibitor N-{3-[3-cyclopropyl-5-(2-fluoro-4-iodophenylamino)6,8-dimethyl;     -2,4,7-trioxo-3,4,6,7-tetrahydro-2H-pyrido[4,3-d]pyrimidin-1-yl]phenyl}acetamide, or a pharmaceutically acceptable salt or solvate thereof, and a PD-1 antagonist; pharmaceutical compositions comprising the same and methods of using such combinations and compositions in the treatment of conditions in which the inhibition of MEK and/or B-Raf and/or immune modulation through PD-1 is beneficial, e.g., cancer.

10 Claims, 10 Drawing Sheets hPD-1.08A light chain CDR1 (SEQ ID NO:1)

Arg Ala Ser Lys Ser Val Ser Thr Ser Gly Phe Ser Tyr Leu His hPD-1.08A light chain CDR2 (SEQ ID NO:2)

Leu Ala Ser Asn Leu Glu Ser hPD-1-08A light chain CDR3 (SEQ ID NO:3)

Gln His Ser Trp Glu Leu Pro Leu Thr hPD-1.08A heavy chain CDR1 (SEQ ID NO:4)

Ser Tyr Tyr Leu Tyr hPD-1.08A heavy chain CDR2 (SEQ ID NO:5)

Gly Val Asn Pro Ser Asn Gly Gly Thr Asn Phe Ser Glu Lys Phe Lys Ser hPD-1.08A heavy chain CDR3 (SEQ ID NO:6)

Arg Asp Ser Asn Tyr Asp Gly Gly Phe Asp Tyr

FIG.1 hPD-1.09A light chain CDR1 (SEQ ID NO:7)

Arg Ala Ser Lys Gly Val Ser Thr Ser Gly Tyr Ser Tyr Leu His hPD-1.09A light chain CDR2 (SEQ ID NO:8)

Leu Ala Ser Tyr Leu Glu Ser hPD-1.09A light chain CDR3 (SEQ ID NO:9)

Gln His Ser Arg Asp Leu Pro Leu Thr hPD-1.09A heavy chain CDR1 (SEQ ID NO:10)

Asn Tyr Tyr Met Tyr hPD-1.09A heavy chain CDR2 (SEQ ID NO:11)

Gly Ile Asn Pro Ser Asn Gly Gly Thr Asn Phe Asn Glu Lys Phe Lys Asn hPD-1.09A heavy chain CDR3 (SEQ ID NO:12)

Arg Asp Tyr Arg Phe Asp Met Gly Phe Asp Tyr

FIG.2

109A-H heavy chain variable region (SEQ ID NO:13)

Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser

409A-H heavy chain full length (SEQ ID NO:14)

Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser Ala Ser Thr Lys Gly Pro Ser Val Phe Pro Leu Ala Pro
Cys Ser Arg Ser Thr Ser Glu Ser Thr Ala Ala Leu Gly Cys Leu Val Lys Asp Tyr
Phe Pro Glu Pro Val Thr Val Ser Trp Asn Ser Gly Ala Leu Thr Ser Gly Val His
Thr Phe Pro Ala Val Leu Gln Ser Ser Gly Leu Tyr Ser Leu Ser Ser Val Val Thr
Val Pro Ser Ser Ser Leu Gly Thr Lys Thr Tyr Thr Cys Asn Val Asp His Lys Pro
Ser Asn Thr Lys Val Asp Lys Arg Val Glu Ser Lys Tyr Gly Pro Pro Cys Pro Pro
Cys Pro Ala Pro Glu Phe Leu Gly Gly Pro Ser Val Phe Leu Phe Pro Pro Lys Pro
Lys Asp Thr Leu Met Ile Ser Arg Thr Pro Glu Val Thr Cys Val Val Val Asp Val
Ser Gln Glu Asp Pro Glu Val Gln Phe Asn Trp Tyr Val Asp Gly Val Glu Val His
Asn Ala Lys Thr Lys Pro Arg Glu Glu Gln Phe Asn Ser Thr Tyr Arg Val Val Ser
Val Leu Thr Val Leu His Gln Asp Trp Leu Asn Gly Lys Glu Tyr Lys Cys Lys Val
Ser Asn Lys Gly Leu Pro Ser Ser Ile Glu Lys Thr Ile Ser Lys Ala Lys Gly Gln
Pro Arg Glu Pro Gln Val Tyr Thr Leu Pro Pro Ser Gln Glu Glu Met Thr Lys Asn
Gln Val Ser Leu Thr Cys Leu Val Lys Gly Phe Tyr Pro Ser Asp Ile Ala Val Glu
Trp Glu Ser Asn Gly Gln Pro Glu Asn Asn Tyr Lys Thr Thr Pro Pro Val Leu Asp
Ser Asp Gly Ser Phe Phe Leu Tyr Ser Arg Leu Thr Val Asp Lys Ser Arg Trp Gln
Glu Gly Asn Val Phe Ser Cys Ser Val Met His Glu Ala Leu His Asn His Tyr Thr
Gln Lys Ser Leu Ser Leu Ser Leu Gly Lys

FIG.3

K09A-L-11 light chain variable region (SEQ ID NO:15)

Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys

K09A-L-16 light chain variable region (SEQ ID NO:16)

Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys

K09A-L-17 light chain variable region (SEQ ID NO:17)

Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys

FIG.4

K09A-L-11 light chain full length (SEQ ID NO:18)

Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

K09A-L-16 light chain full length (SEQ ID NO:19)

Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

FIG.5A

K09A-L-17 light chain full length (SEQ ID NO:20)

Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

Heavy chain (SEQ ID NO:21)

QVQLVQSGVE VKKPGASVKV SCKASGYTFT NYYMYWVRQA PGQGLEWMGG 50
INPSNGGTNF NEKFKNRVTL TTDSSTTTAY MELKSLQFDD TAVYYCARRD 100
YRFDMGFDYW GQGTTVTVSS ASTKGPSVFP LAPCSRSTSE STAALGCLVK 150
DYFPEPVTVS WNSGALTSGV HTFPAVLQSS GLYSLSSVVT VPSSSLGTKT 200
YTCNVDHKPS NTKVDKRVES KYGPPCPPCP APEFLGGPSV FLFPPKPKDT 250
LMISRTPEVT CVVVDVSQED PEVQFNWYVD GVEVHNAKTK PREEQFNSTY 300
RVVSVLTVLH QDWLNGKEYK CKVSNKGLPS SIEKTISKAK GQPREPQVYT 350
LPPSQEEMTK NQVSLTCLVK GFYPSDIAVE WESNGQPENN YKTTPPVLDS 400
DGSFFLYSRL TVDKSRWQEG NVFSCSVMHE ALHNHYTQKS LSLSLGK    447

Light chain (SEQ ID NO:22)

EIVLTQSPAT LSLSPGERAT LSCRASKGVS TSGYSYLHWY QQKPGQAPRL 50
LIYLASYLES GVPARFSGSG SGTDFTLTIS SLEPEDFAVY YCQHSRDLPL 100
TFGGGTKVEI KRTVAAPSVF IFPPSDEQLK SGTASVVCLL NNFYPREAKV 150
QWKVDNALQS GNSQESVTEQ DSKDSTYSLS STLTLSKADY EKHKVYACEV 200
THQGLSSPVT KSFNRGEC                                   219

FIG.6

Nivolumab

Heavy chain (SEQ ID NO:23)

| | | | | | |
|---|---|---|---|---|---|
| QVQLVESGGG | VVQPGRSLRL | DCKASGITFS | NSGMHWVRQA | PGKGLEWVAV | 50 |
| IWYDGSKRYY | ADSVKGRFTI | SRDNSKNTLF | LQMNSLRAED | TAVYYCATND | 100 |
| DYWGQGTLVT | VSSASTKGPS | VFPLAPCSRS | TSESTAALGC | LVKDYFPEPV | 150 |
| TVSWNSGALT | SGVHTFPAVL | QSSGLYSLSS | VVTVPSSSLG | TKTYTCNVDH | 200 |
| KPSNTKVDKR | VESKYGPPCP | PCPAPEFLGG | PSVFLFPPKP | KDTLMISRTP | 250 |
| EVTCVVVDVS | QEDPEVQFNW | YVDGVEVHNA | KTKPREEQFN | STYRVVSVLT | 300 |
| VLHQDWLNGK | EYKCKVSNKG | LPSSIEKTIS | KAKGQPREPQ | VYTLPPSQEE | 350 |
| MTKNQVSLTC | LVKGFYPSDI | AVEWESNGQP | ENNYKTTPPV | LDSDGSFFLY | 400 |
| SRLTVDKSRW | QEGNVFSCSV | MHEALHNHYT | QKSLSLSLGK | | 440 |

Light chain (SEQ ID NO:24)

| | | | | | |
|---|---|---|---|---|---|
| EIVLTQSPAT | LSLSPGERAT | LSCRASQSVS | SYLAWYQQKP | GQAPRLLIYD | 50 |
| ASNRATGIPA | RFSGSGSGTD | FTLTISSLEP | EDFAVYYCQQ | SSNWPRTFGQ | 100 |
| GTKVEIKRTV | AAPSVFIFPP | SDEQLKSGTA | SVVCLLNNFY | PREAKVQWKV | 150 |
| DNALQSGNSQ | ESVTEQDSKD | STYSLSSTLT | LSKADYEKHK | VYACEVTHQG | 200 |
| LSSPVTKSFN | RGEC | | | | 214 |

FIG.7

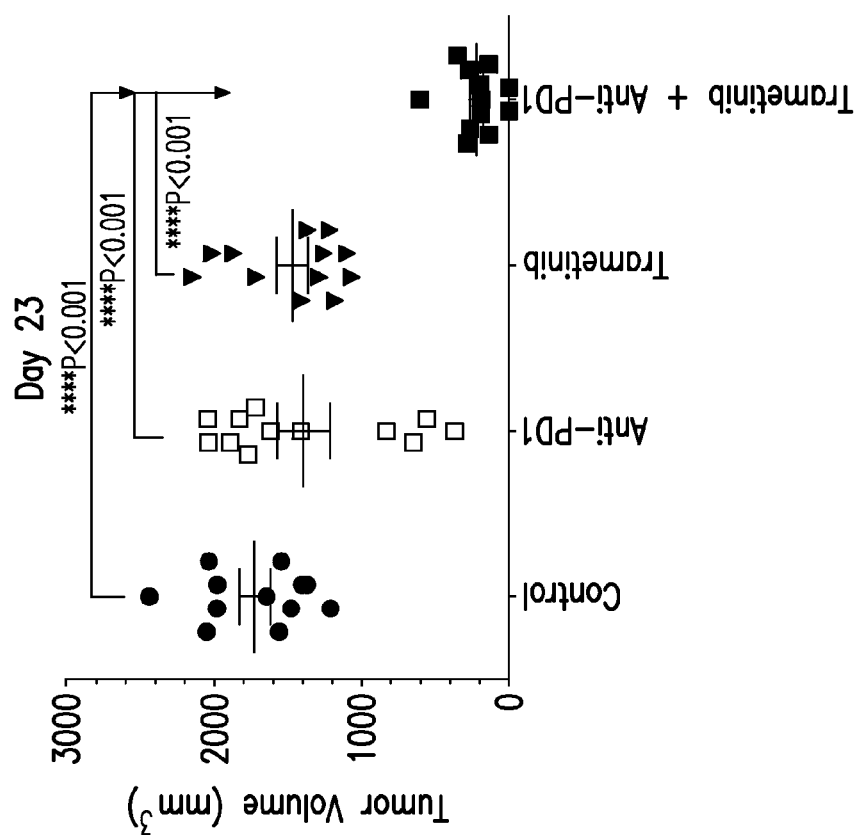
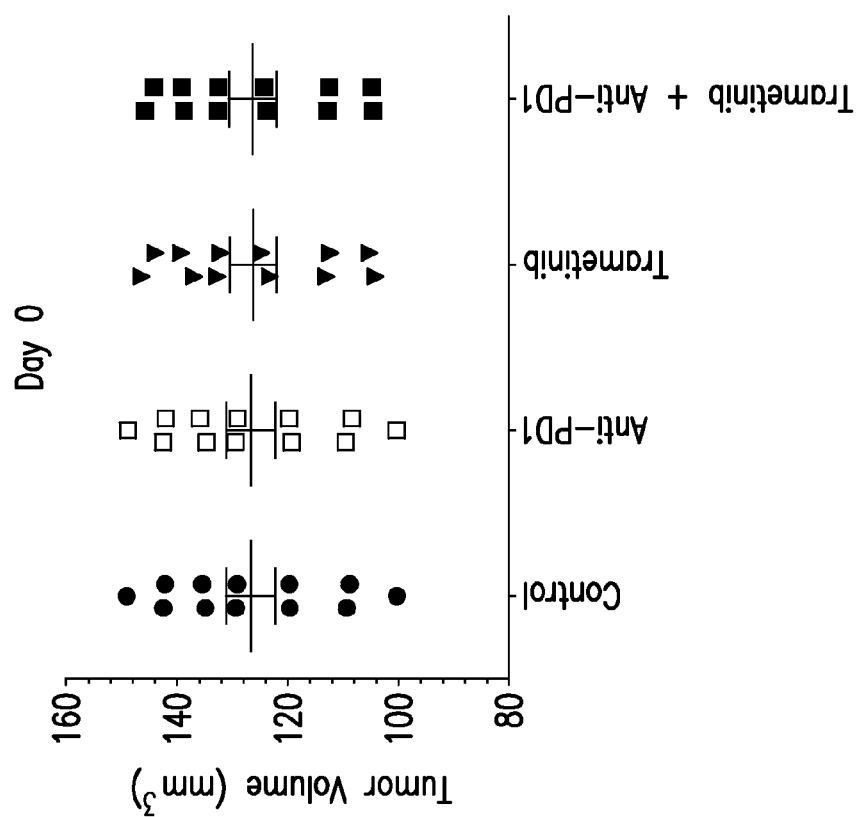
FIG. 8B

SEQUENCE LISTING

```
<160> NUMBER OF SEQ ID NOS: 25

<210> SEQ ID NO 1
<211> LENGTH: 15
<212> TYPE: PRT
<213> ORGANISM: Artificial
<220> FEATURE:
<223> OTHER INFORMATION: Antibody Light Chain CDR

<400> SEQUENCE: 1

Arg Ala Ser Lys Ser Val Ser Thr Ser Gly Phe Ser Tyr Leu His
1               5                   10                  15

<210> SEQ ID NO 2
<211> LENGTH: 7
<212> TYPE: PRT
<213> ORGANISM: Artificial
<220> FEATURE:
<223> OTHER INFORMATION: Antibody Light Chain CDR

<400> SEQUENCE: 2

Leu Ala Ser Asn Leu Glu Ser
1               5

<210> SEQ ID NO 3
```

```
<211> LENGTH: 9
<212> TYPE: PRT
<213> ORGANISM: Artificial
<220> FEATURE:
<223> OTHER INFORMATION: Antibody Light Chain CDR

<400> SEQUENCE: 3

Gln His Ser Trp Glu Leu Pro Leu Thr
1               5

<210> SEQ ID NO 4
<211> LENGTH: 5
<212> TYPE: PRT
<213> ORGANISM: Artificial
<220> FEATURE:
<223> OTHER INFORMATION: Antibody Heavy Chain CDR

<400> SEQUENCE: 4

Ser Tyr Tyr Leu Tyr
1               5

<210> SEQ ID NO 5
<211> LENGTH: 17
<212> TYPE: PRT
<213> ORGANISM: Artificial
<220> FEATURE:
<223> OTHER INFORMATION: Antibody Heavy Chain CDR

<400> SEQUENCE: 5

Gly Val Asn Pro Ser Asn Gly Gly Thr Asn Phe Ser Glu Lys Phe Lys
1               5                   10                  15

Ser

<210> SEQ ID NO 6
<211> LENGTH: 11
<212> TYPE: PRT
<213> ORGANISM: Artificial
<220> FEATURE:
<223> OTHER INFORMATION: Antibody Heavy Chain CDR

<400> SEQUENCE: 6

Arg Asp Ser Asn Tyr Asp Gly Gly Phe Asp Tyr
1               5                   10

<210> SEQ ID NO 7
<211> LENGTH: 15
<212> TYPE: PRT
<213> ORGANISM: Artificial
<220> FEATURE:
<223> OTHER INFORMATION: Antibody Light Chain CDR

<400> SEQUENCE: 7

Arg Ala Ser Lys Gly Val Ser Thr Ser Gly Tyr Ser Tyr Leu His
1               5                   10                  15

<210> SEQ ID NO 8
<211> LENGTH: 7
<212> TYPE: PRT
<213> ORGANISM: Artificial
<220> FEATURE:
<223> OTHER INFORMATION: Antibody Light Chain CDR

<400> SEQUENCE: 8

Leu Ala Ser Tyr Leu Glu Ser
1               5
```

```
<210> SEQ ID NO 9
<211> LENGTH: 9
<212> TYPE: PRT
<213> ORGANISM: Artificial
<220> FEATURE:
<223> OTHER INFORMATION: Antibody Light Chain CDR

<400> SEQUENCE: 9

Gln His Ser Arg Asp Leu Pro Leu Thr
1               5

<210> SEQ ID NO 10
<211> LENGTH: 5
<212> TYPE: PRT
<213> ORGANISM: Artificial
<220> FEATURE:
<223> OTHER INFORMATION: Antibody Heavy Chain CDR

<400> SEQUENCE: 10

Asn Tyr Tyr Met Tyr
1               5

<210> SEQ ID NO 11
<211> LENGTH: 17
<212> TYPE: PRT
<213> ORGANISM: Artificial
<220> FEATURE:
<223> OTHER INFORMATION: Antibody Heavy Chain CDR

<400> SEQUENCE: 11

Gly Ile Asn Pro Ser Asn Gly Gly Thr Asn Phe Asn Glu Lys Phe Lys
1               5                   10                  15

Asn

<210> SEQ ID NO 12
<211> LENGTH: 11
<212> TYPE: PRT
<213> ORGANISM: Artificial
<220> FEATURE:
<223> OTHER INFORMATION: Antibody Heavy Chain CDR

<400> SEQUENCE: 12

Arg Asp Tyr Arg Phe Asp Met Gly Phe Asp Tyr
1               5                   10

<210> SEQ ID NO 13
<211> LENGTH: 120
<212> TYPE: PRT
<213> ORGANISM: Artificial
<220> FEATURE:
<223> OTHER INFORMATION: Humanized Antibody Heavy Chain Variable Region

<400> SEQUENCE: 13

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
```

```
                              85                  90                  95

Ala Arg Arg Asp Tyr Arg Phe Asp Met Gly Phe Asp Tyr Trp Gly Gln
                100                 105                 110

Gly Thr Thr Val Thr Val Ser Ser
            115                 120

<210> SEQ ID NO 14
<211> LENGTH: 447
<212> TYPE: PRT
<213> ORGANISM: Artificial
<220> FEATURE:
<223> OTHER INFORMATION: Humanized Antibody Heavy Chain

<400> SEQUENCE: 14

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
```

325                 330                 335
Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 15
<211> LENGTH: 111
<212> TYPE: PRT
<213> ORGANISM: Artificial
<220> FEATURE:
<223> OTHER INFORMATION: Humanized Antibody Light Chain Variable Region

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 16
<211> LENGTH: 111
<212> TYPE: PRT
<213> ORGANISM: Artificial
<220> FEATURE:
<223> OTHER INFORMATION: Humanized Antibody Light Chain Variable Region

<400> SEQUENCE: 16

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys
            100                 105                 110

<210> SEQ ID NO 17
<211> LENGTH: 111
<212> TYPE: PRT
<213> ORGANISM: Artificial
<220> FEATURE:
<223> OTHER INFORMATION: Humanized Antibody Light Chain Variable Regon

<400> SEQUENCE: 17

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys
            100                 105                 110

<210> SEQ ID NO 18
<211> LENGTH: 218
<212> TYPE: PRT
<213> ORGANISM: Artificial
<220> FEATURE:
<223> OTHER INFORMATION: Humanzed Antiboy LIght Chain

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 19
<211> LENGTH: 218
<212> TYPE: PRT
<213> ORGANISM: Artificial
<220> FEATURE:
<223> OTHER INFORMATION: Humanized Antibody Light Chain

<400> SEQUENCE: 19

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 20
<211> LENGTH: 218
<212> TYPE: PRT
<213> ORGANISM: Artificial
<220> FEATURE:
<223> OTHER INFORMATION: Humanized Antibody Light Chain

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro

```
                    35                  40                  45
Gln Leu Leu Ile Tyr Leu Ala Ser Tyr Leu Glu Ser Gly Val Pro Asp
 50                  55                  60

Arg Phe Ser Gly Ser Gly Ser Gly Thr Ala Phe Thr Leu Lys Ile Ser
 65                  70                  75                  80

Arg Val Glu Ala Glu Asp Val Gly Leu Tyr Tyr Cys Gln His Ser Arg
                 85                  90                  95

Asp Leu Pro Leu Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 21
<211> LENGTH: 447
<212> TYPE: PRT
<213> ORGANISM: Artificial
<220> FEATURE:
<223> OTHER INFORMATION: Humanized Antibody Heavy Chain

<400> SEQUENCE: 21

Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Tyr Met Tyr Trp Val Arg Gln Ala Pro Gly Gln Gly Leu Glu Trp Met
         35                  40                  45

Gly Gly Ile Asn Pro Ser Asn Gly Gly Thr Asn Phe Asn Glu Lys Phe
 50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
                180             185             190
Ser Ser Ser Leu Gly Thr Lys Thr Tyr Thr Cys Asn Val Asp His Lys
            195             200             205

Pro Ser Asn Thr Lys Val Asp Lys Arg Val Glu Ser Lys Tyr Gly Pro
        210             215             220

Pro Cys Pro Pro Cys Pro Ala Pro Glu Phe Leu Gly Gly Pro Ser Val
225             230             235             240

Phe Leu Phe Pro Pro Lys Pro Lys Asp Thr Leu Met Ile Ser Arg Thr
            245             250             255

Pro Glu Val Thr Cys Val Val Val Asp Val Ser Gln Glu Asp Pro Glu
        260             265             270

Val Gln Phe Asn Trp Tyr Val Asp Gly Val Glu Val His Asn Ala Lys
            275             280             285

Thr Lys Pro Arg Glu Glu Gln Phe Asn Ser Thr Tyr Arg Val Val Ser
        290             295             300

Val Leu Thr Val Leu His Gln Asp Trp Leu Asn Gly Lys Glu Tyr Lys
305             310             315             320

Cys Lys Val Ser Asn Lys Gly Leu Pro Ser Ser Ile Glu Lys Thr Ile
            325             330             335

Ser Lys Ala Lys Gly Gln Pro Arg Glu Pro Gln Val Tyr Thr Leu Pro
        340             345             350

Pro Ser Gln Glu Glu Met Thr Lys Asn Gln Val Ser Leu Thr Cys Leu
            355             360             365

Val Lys Gly Phe Tyr Pro Ser Asp Ile Ala Val Glu Trp Glu Ser Asn
370             375             380

Gly Gln Pro Glu Asn Asn Tyr Lys Thr Thr Pro Pro Val Leu Asp Ser
385             390             395             400

Asp Gly Ser Phe Phe Leu Tyr Ser Arg Leu Thr Val Asp Lys Ser Arg
            405             410             415

Trp Gln Glu Gly Asn Val Phe Ser Cys Ser Val Met His Glu Ala Leu
        420             425             430

His Asn His Tyr Thr Gln Lys Ser Leu Ser Leu Ser Leu Gly Lys
            435             440             445

<210> SEQ ID NO 22
<211> LENGTH: 218
<212> TYPE: PRT
<213> ORGANISM: Artificial
<220> FEATURE:
<223> OTHER INFORMATION: Humanized Antibody Light Chain

<400> SEQUENCE: 22

Glu Ile Val Leu Thr Gln Ser Pro Ala Thr Leu Ser Leu Ser Pro Gly
1               5               10              15

Glu Arg Ala Thr Leu Ser Cys Arg Ala Ser Lys Gly Val Ser Thr Ser
            20              25              30

Gly Tyr Ser Tyr Leu His Trp Tyr Gln Gln Lys Pro Gly Gln Ala Pro
        35              40              45

Arg Leu Leu Ile Tyr Leu Ala Ser Tyr Leu Glu Ser Gly Val Pro Ala
    50              55              60

Arg Phe Ser Gly Ser Gly Ser Gly Thr Asp Phe Thr Leu Thr Ile Ser
65              70              75              80

Ser Leu Glu Pro Glu Asp Phe Ala Val Tyr Tyr Cys Gln His Ser Arg
            85              90              95

Asp Leu Pro Leu Thr Phe Gly Gly Gly Thr Lys Val Glu Ile Lys Arg
```

```
                    100                 105                 110
Thr Val Ala Ala Pro Ser Val Phe Ile Phe Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
                210                 215

<210> SEQ ID NO 23
<211> LENGTH: 440
<212> TYPE: PRT
<213> ORGANISM: Homo sapiens

<400> SEQUENCE: 23

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
                100                 105                 110

Ser Ala Ser Thr Lys Gly Pro Ser Val Phe Pro Leu Ala Pro Cys Ser
                115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
                180                 185                 190

Thr Tyr Thr Cys Asn Val Asp His Lys Pro Ser Asn Thr Lys Val Asp
                195                 200                 205

Lys Arg Val Glu Ser Lys Tyr Gly Pro Pro Cys Pro Pro Cys Pro Ala
                210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255
```

```
Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 24
<211> LENGTH: 214
<212> TYPE: PRT
<213> ORGANISM: Homo sapiens

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 290
<212> TYPE: PRT
<213> ORGANISM: Homo sapiens
<220> FEATURE:
<221> NAME/KEY: mat_peptide
<222> LOCATION: (19)..(290)

<400> SEQUENCE: 25

Met Arg Ile Phe Ala Val Phe Ile Phe Met Thr Tyr Trp His Leu Leu
            -15                 -10                 -5

Asn Ala Phe Thr Val Thr Val Pro Lys Asp Leu Tyr Val Val Glu Tyr
    -1  1               5                   10

Gly Ser Asn Met Thr Ile Glu Cys Lys Phe Pro Val Glu Lys Gln Leu
 15              20                  25                      30

Asp Leu Ala Ala Leu Ile Val Tyr Trp Glu Met Glu Asp Lys Asn Ile
             35                  40                  45

Ile Gln Phe Val His Gly Glu Glu Asp Leu Lys Val Gln His Ser Ser
            50                  55                  60

Tyr Arg Gln Arg Ala Arg Leu Leu Lys Asp Gln Leu Ser Leu Gly Asn
            65                  70                  75

Ala Ala Leu Gln Ile Thr Asp Val Lys Leu Gln Asp Ala Gly Val Tyr
 80              85                  90

Arg Cys Met Ile Ser Tyr Gly Gly Ala Asp Tyr Lys Arg Ile Thr Val
 95              100                 105                 110

Lys Val Asn Ala Pro Tyr Asn Lys Ile Asn Gln Arg Ile Leu Val Val
                115                 120                 125

Asp Pro Val Thr Ser Glu His Glu Leu Thr Cys Gln Ala Glu Gly Tyr
            130                 135                 140

Pro Lys Ala Glu Val Ile Trp Thr Ser Ser Asp His Gln Val Leu Ser
            145                 150                 155

Gly Lys Thr Thr Thr Thr Asn Ser Lys Arg Glu Glu Lys Leu Phe Asn
    160                 165                 170

Val Thr Ser Thr Leu Arg Ile Asn Thr Thr Thr Asn Glu Ile Phe Tyr
175                 180                 185                 190

Cys Thr Phe Arg Arg Leu Asp Pro Glu Glu Asn His Thr Ala Glu Leu
            195                 200                 205

Val Ile Pro Glu Leu Pro Leu Ala His Pro Pro Asn Glu Arg Thr His
            210                 215                 220

Leu Val Ile Leu Gly Ala Ile Leu Leu Cys Leu Gly Val Ala Leu Thr
            225                 230                 235

Phe Ile Phe Arg Leu Arg Lys Gly Arg Met Met Asp Val Lys Lys Cys
            240                 245                 250

Gly Ile Gln Asp Thr Asn Ser Lys Lys Gln Ser Asp Thr His Leu Glu
255                 260                 265                 270

Glu Thr
```

COMBINATION THERAPIES FOR CANCER

RELATED APPLICATIONS

This application is a 35 U.S.C. § 371 filing of International Application No. PCT/US2014/039686, filed May 28, 2014, which claims priority to U.S. Patent Application Nos. 61/829,472, filed May 31, 2013, 61/873,476, filed Sep. 4, 2013 and 61/981,906, filed Apr. 21, 2014, the contents of each of which are incorporated herein by reference in their entireties.

FIELD OF THE INVENTION

The present invention relates to a method of treating cancer in a mammal and to combinations useful in such treatment. In particular, the method relates to a novel combination comprising a B-Raf inhibitor, particularly N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and/or the MEK inhibitor N-{3-[3-cyclopropyl-5-(2-fluoro-4-iodophenylamino)6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate thereof, and a PD-1 antagonist (e.g., an anti-PD-1 antibody or antigen binding fragment thereof, or an anti-PD-Ligand antibody or antigen binding fragment thereof); pharmaceutical compositions comprising the same and methods of using such combinations and compositions in the treatment of conditions in which the inhibition of MEK and/or inhibition of B-Raf and/or inhibiting endogenous PD-L1 and/or PD-L2 from binding PD-1 is beneficial, e.g., cancer.

BACKGROUND OF THE INVENTION

Effective treatment of hyperproliferative disorders including cancer is a continuing goal in the oncology field. Generally, cancer results from the deregulation of the normal processes that control cell division, differentiation and apoptotic cell death and is characterized by the proliferation of malignant cells which have the potential for unlimited growth, local expansion and systemic metastasis. Deregulation of normal processes include abnormalities in signal transduction pathways and response to factors which differ from those found in normal cells.

An important large family of enzymes is the protein kinase enzyme family. Currently, there are about 500 different known protein kinases. Protein kinases serve to catalyze the phosphorylation of an amino acid side chain in various proteins by the transfer of the γ-phosphate of the ATP-Mg$^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins.

Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity including benign and malignant proliferative disorders as well as diseases resulting from inappropriate activation of the immune and nervous systems. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The protein serine/threonine kinases (PSTK), includes cyclic AMP- and cyclic GMP-dependent protein kinases, calcium and phospholipid dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also in progress to identify modulators of tyrosine kinases as well.

Receptor tyrosine kinases (RTKs) catalyze phosphorylation of certain tyrosyl amino acid residues in various proteins, including themselves, which govern cell growth, proliferation and differentiation.

Downstream of the several RTKs lie several signaling pathways, among them is the Ras-Raf-MEK-ERK kinase pathway. It is currently understood that activation of Ras GTPase proteins in response to growth factors, hormones, cytokines, etc. stimulates phosphorylation and activation of Raf kinases. These kinases then phosphorylate and activate the intracellular protein kinases MEK1 and MEK2, which in turn phosphorylate and activate other protein kinases, ERK1 and 2. This signaling pathway, also known as the mitogen-activated protein kinase (MAPK) pathway or cytoplasmic cascade, mediates cellular responses to growth signals. The ultimate function of this pathway is to link receptor activity at the cell membrane with modification of cytoplasmic or nuclear targets that govern cell proliferation, differentiation, and survival.

The constitutive activation of this pathway is sufficient to induce cellular transformation. Disregulated activation of the MAP kinase pathway, due to aberrant receptor tyrosine kinase activation, Ras mutations or Raf mutations, has frequently been found in human cancers, and represents a major factor determining abnormal growth control. In human malignances, Ras mutations are common, having been identified in about 30% of cancers. The Ras family of GTPase proteins (proteins which convert guanosine triphosphate to guanosine diphosphate) relay signals from activated growth factor receptors to downstream intracellular partners. Prominent among the targets recruited by active membrane-bound Ras are the Raf family of serine/threonine protein kinases. The Raf family is composed of three related kinases (A-, B- and C-Raf) that act as downstream effectors of Ras. Ras-mediated Raf activation in turn triggers activation of MEK1 and MEK2 (MAP/ERK kinases 1 and 2), which in turn phosphorylate ERK1 and ERK2 (extracellular signal-regulated kinases 1 and 2) on tyrosine-185 and threonine-183. Activated ERK1 and ERK2 translocate and accumulate in the nucleus, where they can phosphorylate a variety of substrates, including transcription factors that control cellular growth and survival. Given the importance of the Ras/Raf/MEK/ERK pathway in the development of human cancers, the kinase components of the signaling cascade are merging as potentially important targets for the modulation of disease progression in cancer and other proliferative diseases.

MEK1 and MEK2 are members of a larger family of dual-specificity kinases (MEK1-7) that phosphorylate threonine and tyrosine residues of various MAP kinases. MEK1 and MEK2 are encoded by distinct genes, but they share high homology (80%) both within the C-terminal catalytic kinase domains and the most of the N-terminal regulatory region. Oncogenic forms of MEK1 and MEK2 have not been found in human cancers, but constitutive activation of MEK has been shown to result in cellular transformation. In addition to Raf, MEK can also be activated by other oncogenes as well. So far, the only known substrates of MEK1 and MEK2 are ERK1 and ERK2. This unusual substrate specificity in addition to the unique ability to phosphorylate both tyrosine and threonine residues places MEK1 and MEK2 at a critical point in the signal transduction cascade which allows these MEK proteins to integrate many extracellular signals into the MAPK pathway.

Accordingly, it has been recognized that an inhibitor of a protein of the MAPK kinase pathway (eg. MEK) should be of value both as an anti-proliferative, pro-apoptotic and anti-invasive agent for use in the containment and/or treatment of proliferative or invasive disease.

Moreover, it is also known that a compound having MEK inhibitory activity effectively induces inhibition of ERK1/2 activity and suppression of cell proliferation (The Journal of Biological Chemistry, vol. 276, No. 4 pp. 2686-2692, 2001), and the compound is expected to show effects on diseases caused by undesirable cell proliferation, such as tumor genesis and/or cancer. Mutations in various Ras GTPases and the B-Raf kinase have been identified that can lead to sustained and constitutive activation of the MAPK pathway, ultimately resulting in increased cell division and survival. These mutations have been strongly linked with the establishment, development, and progression of a wide range of human cancers. For example, in melanoma, more than 80% of the BRAF mutations cause a substitution of the amino acid glutamate (E) for valine (V) at position 600 (V600E) of the BRAF protein, whereas approximately 3-20% of melanoma mutations are a substitution of lysine (K) for valine at position 600 (V600K) (Gorden et al., Cancer Res (2003) 63:3955-3957; Houben et al., J Carcinog (2004) 3:6; Kumar et al., Clin Cancer Res. (2003) 9:3362-3368; Libra et al., Cell Cycle (2005) 4:1382-1384; Omholt et al. Clin Cancer Res (2003) 9:6483-6488. The biological role of the Raf kinases, and specifically that of B-Raf, in signal transduction is described in Davies, H., et al., Nature (2002) 9:1-6; Garnett, M. J. & Marais, R., Cancer Cell (2004) 6:313-319; Zebisch, A. & Troppmair, J., Cell. Mol. Life Sci. (2006) 63:1314-1330; Midgley, R. S. & Kerr, D. J., Crit. Rev. Onc/Hematol. (2002) 44:109-120; Smith, R. A., et al., Curr. Top. Med. Chem. (2006) 6:1071-1089; and Downward, J., Nat. Rev. Cancer (2003) 3:11-22.

Naturally occurring mutations of the B-Raf kinase that activate MAPK pathway signaling have been found in a large percentage of human melanomas (Davies (2002) supra) and thyroid cancers (Cohen et al J. Nat. Cancer Inst. (2003) 95(8) 625-627 and Kimura et al Cancer Res. (2003) 63(7) 1454-1457), as well as at lower, but still significant, frequencies in the following:

Barret's adenocarcinoma (Garnett et al., Cancer Cell (2004) 6 313-319 and Sommerer et al Oncogene (2004) 23(2) 554-558), billiary tract carcinomas (Zebisch et al., Cell. Mol. Life Sci. (2006) 63 1314-1330), breast cancer (Davies (2002) supra), cervical cancer (Moreno-Bueno et al Clin. Cancer Res. (2006) 12(12) 3865-3866), cholangiocarcinoma (Tannapfel et al Gut (2003) 52(5) 706-712), central nervous system tumors including primary CNS tumors such as glioblastomas, astrocytomas and ependymomas (Knobbe et al Acta Neuropathol. (Berl.) (2004) 108(6) 467-470, Davies (2002) supra, and Garnett et al., Cancer Cell (2004) supra) and secondary CNS tumors (i.e., metastases to the central nervous system of tumors originating outside of the central nervous system), colorectal cancer, including large intestinal colon carcinoma (Yuen et al Cancer Res. (2002) 62(22) 6451-6455, Davies (2002) supra and Zebisch et al., Cell. Mol. Life Sci. (2006), gastric cancer (Lee et al Oncogene (2003) 22(44) 6942-6945), carcinoma of the head and neck including squamous cell carcinoma of the head and neck (Cohen et al J. Nat. Cancer Inst. (2003) 95(8) 625-627 and Weber et al Oncogene (2003) 22(30) 4757-4759), hematologic cancers including leukemias (Garnett et al., Cancer Cell (2004) supra, particularly acute lymphoblastic leukemia (Garnett et al., Cancer Cell (2004) supra and Gustafsson et al Leukemia (2005) 19(2) 310-312), acute myelogenous leukemia (AML) (Lee et al Leukemia (2004) 18(1) 170-172, and Christiansen et al Leukemia (2005) 19(12) 2232-2240), myelodysplastic syndromes (Christiansen et al Leukemia (2005) supra) and chronic myelogenous leukemia (Mizuchi et al Biochem. Biophys. Res. Commun. (2005) 326(3) 645-651); Hodgkin's lymphoma (Figl et al Arch. Dermatol. (2007) 143(4) 495-499), non-Hodgkin's lymphoma (Lee et al Br. J. Cancer (2003) 89(10) 1958-1960), megakaryoblastic leukemia (Eychene et al Oncogene (1995) 10(6) 1159-1165) and multiple myeloma (Ng et al Br. J. Haematol. (2003) 123(4) 637-645), hepatocellular carcinoma (Garnett et al., Cancer Cell (2004), lung cancer (Brose et al Cancer Res. (2002) 62(23) 6997-7000, Cohen et al J. Nat. Cancer Inst. (2003) supra and Davies (2002) supra), including small cell lung cancer (Pardo et al EMBO J. (2006) 25(13) 3078-3088) and non-small cell lung cancer (Davies (2002) supra), ovarian cancer (Russell & McCluggage J. Pathol. (2004) 203(2) 617-619 and Davies (2002) supr), endometrial cancer (Garnett et al., Cancer Cell (2004) supra, and Moreno-Bueno et al Clin. Cancer Res. (2006) supra), pancreatic cancer (Ishimura et al Cancer Lett. (2003) 199(2) 169-173), pituitary adenoma (De Martino et al J. Endocrinol. Invest. (2007) 30(1) RC1-3), prostate cancer (Cho et al Int. J. Cancer (2006) 119(8) 1858-1862), renal cancer (Nagy et al Int. J. Cancer (2003) 106(6) 980-981), sarcoma (Davies (2002) supra), and skin cancers (Rodriguez-Viciana et al Science (2006) 311(5765) 1287-1290 and Davies (2002) supra). Overexpression of c-Raf has been linked to AML (Zebisch et al., Cancer Res. (2006) 66(7) 3401-3408, and Zebisch (Cell. Mol. Life Sci. (2006)) and erythroleukemia (Zebisch et al., Cell. Mol. Life Sci. (2006).

By virtue of the role played by the Raf family kinases in these cancers and exploratory studies with a range of preclinical and therapeutic agents, including one selectively targeted to inhibition of B-Raf kinase activity (King A. J., et al., (2006) *Cancer Res.* 66:11100-11105), it is generally accepted that inhibitors of one or more Raf family kinases will be useful for the treatment of such cancers or other condition associated with Raf kinase.

Mutation of B-Raf has also been implicated in other conditions, including cardio-facio cutaneous syndrome (Rodriguez-Viciana et al *Science* (2006) 311(5765) 1287-1290) and polycystic kidney disease (Nagao et al *Kidney Int.* (2003) 63(2) 427-437).

Programmed Cell Death 1 (PD-1) is a 50-55 kDa type I transmembrane receptor originally identified by subtractive hybridization of a mouse T cell line undergoing apoptosis (Ishida et al., 1992, *Embo J.* 11:3887-95). A member of the CD28 gene family, PD-1 is expressed on activated T, B, and myeloid lineage cells (Greenwald et al., 2005, *Annu. Rev. Immunol.* 23:515-48; Sharpe et al., 2007, Nat. Immunol. 8:239-45).

U.S. Pat. Nos. 6,808,710 and 7,101,550, issued to C. Wood and G. Freeman on Oct. 26, 2004 and Sep. 5, 2006, respectively, disclose methods for attempting to modulate an immune response by activating or inhibiting signaling of the PD-1 receptor using, for example, an antibody that binds PD-1.

Based on the observation that blocking PD-1 inhibitory signals at time of priming decreases immune cell responsiveness, U.S. Pat. No. 7,029,674, issued Apr. 18, 2006 to B. Carreno and J. Leonard, discloses methods to decrease activation of an immune cell by contacting the cell with an agent that inhibits PD-1 signaling. Additionally, U.S. Pat. No. 7,595,048 and U.S. Pat. No. 8,168,179 disclose methods of treating cancer with anti-PD-1 antibodies.

The PD-1 pathway has been of considerable interest to researchers developing therapies to treat melanoma and other tumor types. The PD-1 receptor is expressed on the surface of activated T cells and binds to ligands on the surface of antigen-presenting cells (PD-L1 and PD-L2), an interaction that modulates immune response. Many cancer cells express high levels of PD-L1 on their surface, which cause T cells to switch off through PD-L1's interaction with PD-1, rendering them unable to generate an antitumor response.

PD-1 negatively modulates T cell activation, and this inhibitory function is linked to an immunoreceptor tyrosine-based inhibitory motif (ITIM) of its cytoplasmic domain (Greenwald et al., supra; Parry et al., 2005, *Mol. Cell. Biol.* 25:9543-53). Disruption of this inhibitory function of PD-1 can lead to autoimmunity. For example, PD-1 knockout in C57B1/6 mice leads to a lupus-like syndrome, whereas in BALB/c mice it leads to development of dilated cardiomyopathy (Nishimura et al., 1999, *Immunity* 11:141-51; Okazaki et al., 2003, *Nat. Med.* 9:1477-83). In humans, a single nucleotide polymorphism in PD-1 gene locus is associated with higher incidences of systemic lupus erythematosus, type 1 diabetes, rheumatoid arthritis, and progression of multiple sclerosis. The reverse scenario can also be deleterious. Sustained negative signals by PD-1 have been implicated in T cell dysfunctions in many pathologic situations, such as tumor immune evasion and chronic viral infections.

Host anti-tumor immunity is mainly affected by tumor-infiltrating lymphocytes (TILs) (Galore et al., 2006, *Science* 313:1960-4). Multiple lines of evidence have indicated that TILs are subject to PD-1 inhibitory regulation. First, PD-L1 expression is confirmed in many human and mouse tumor lines and the expression can be further upregulated by IFN-.gamma. in vitro (Dong et al., 2002, Nat. Med. 8:793-800). Second, expression of PD-L1 by tumor cells has been directly associated with their resistance to lysis by anti-tumor T cells in vitro (Dong et al., supra; Blank et al., 2004, Cancer Res. 64:1140-5). Third, PD-1 knockout mice are resistant to tumor challenge (Iwai et al., 2005, Int. Immunol. 17:133-44) and T cells from PD-1 knockout mice are highly effective in tumor rejection when adoptively transferred to tumor-bearing mice (Blank et al., supra). Fourth, blocking PD-1 inhibitory signals by a monoclonal antibody can potentiate host anti-tumor immunity in mice (Iwai et al., supra; Hirano et al., 2005, *Cancer Res.* 65:1089-96). Fifth, high degrees of PD-L1 expression in tumors (detected by immunohistochemical staining) are associated with poor prognosis for many human cancer types (Hamanishi et al., 2007, *Proc. Natl. Acad. Sci. USA* 104:3360-5).

Though there have been many recent advances in the treatment of cancer, there remains a need for more effective and/or enhanced treatment of an individual suffering the effects of cancer. The current invention addresses this need.

SUMMARY OF THE INVENTION

The current invention is directed to a combination of a B-Raf inhibitor, and/or a MEK inhibitor, and an anti-PD-1 antibody or antigen binding fragment thereof in the treatment of cancer.

The present invention is directed to a combination of therapeutic agents that is advantageous over treatment with each agent when administered alone and advantageous over treatment with a combination of a MEK inhibitor and a B-RAF inhibitor. In particular, the drug combination that includes the B-Raf inhibitor N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, and/or the MEK inhibitor N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate thereof, and a PD-1 antagonist (e.g., MK-3475 or an antigen binding fragment thereof) is described.

The MEK inhibitor of the invention is represented by the structure of structure (I):

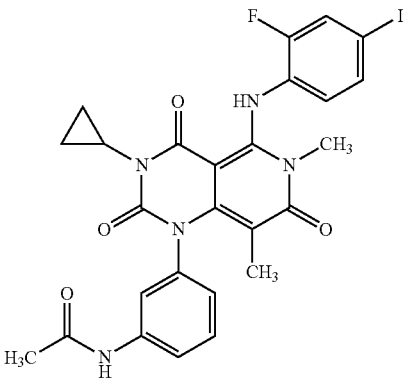 [SMILES: CC(=O)Nc1cccc(-n2c(=O)n(C3CC3)c(=O)c3c(Nc4ccc(I)cc4F)n(C)c(=O)c(C)c32)c1]

or a pharmaceutically acceptable salt or solvate thereof (collectively referred to herein as "Compound A"), The B-Raf inhibitor of the invention is represented by the structure of structure (II):

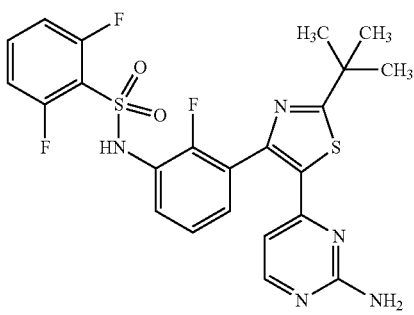 [SMILES: CC(C)(C)c1nc(-c2cccc(NS(=O)(=O)c3c(F)cccc3F)c2F)c(-c2ccnc(N)n2)s1]

or a pharmaceutically acceptable salt thereof (collectively referred to herein as "Compound B").

The PD-1 antagonist of the invention inhibits the binding of PD-L1 to PD-1, and preferably also inhibits the binding of PD-L2 to PD-1. Preferably, the PD-1 antagonist is a monoclonal antibody, or an antigen binding fragment thereof, which specifically binds to PD-1 and blocks the binding of PD-L1 to PD-1. In one particularly preferred embodiment, the PD-1 antagonist is an anti-PD-1 monoclonal antibody that binds to PD-1 and blocks binding of both PD-L1 and PD-L2 to PD-1.

Nivolumab, which is also known as BMS-936558 and MDX1106, is a fully human IgG4 monoclonal antibody which binds to PD-1 and is designed for the treatment of cancer by Bristol-Myers Squibb and Ono Pharmaceuticals.

MK-3475, which was previously known as lambrolizumab, is a humanized IgG4 monoclonal antibody which binds to PD-1 and is being developed by Merck and Co for the treatment of cancer.

In a first aspect of the present invention, there is provided a combination comprising a PD-1 antagonist and one or both of a Compound A and a Compound B, wherein:
the Compound B is a compound of structure (II)

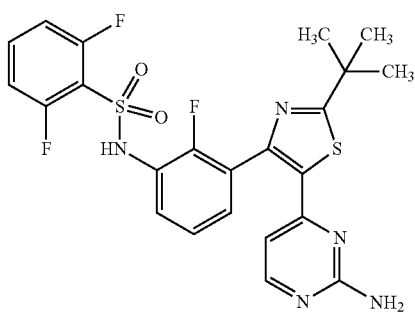

or a pharmaceutically acceptable salt thereof; and
the Compound A is a compound of structure (I):

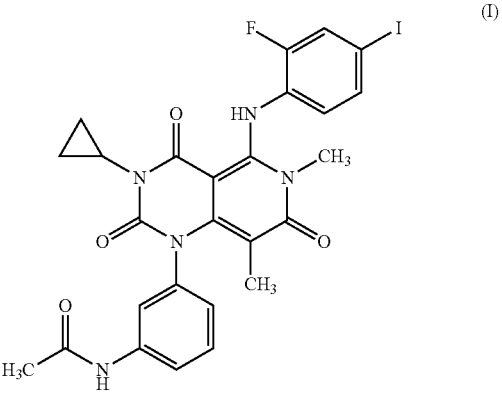 [SMILES: CC(=O)Nc1cccc(-n2c(=O)n(C3CC3)c(=O)c3c(Nc4ccc(I)cc4F)n(C)c(=O)c(C)c32)c1]

or a pharmaceutically acceptable salt or solvate thereof.

In another aspect of the invention, there is provided a combination comprising a PD-1 antagonist and one or both of a Compound A and a Compound B, wherein the Compound B is N-{3-[5-(2-Amino-4-pyrimidinyl)-2-(1,1-dimethylethyl)-1,3-thiazol-4-yl]-2-fluorophenyl}-2,6-difluorobenzenesulfonamide methanesulfonate; and the Compound A is N-{3-[3-cyclopropyl-5-(2-fluoro-4-iodophenylamino)6,8-dimethyl-2,4,7-trioxo-3,4,6,7-tetrahydro-2H-pyrido[4,3-d]pyrimidin-1-yl]phenyl}acetamide dimethyl sulfoxide (solvate).

In another aspect of the present invention, there is provided a combination, comprising a PD-1 antagonist and one or both of a Compound A and a Compound B for use in therapy, wherein:
the Compound B is a compound of structure (II):

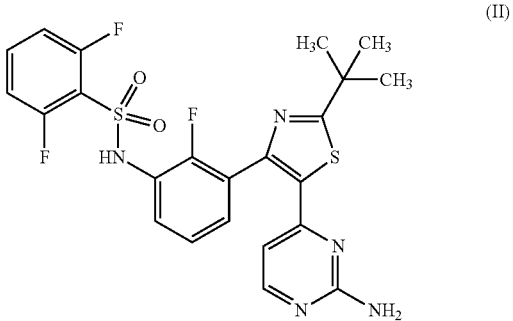 [SMILES: CC(C)(C)c1nc(-c2cccc(NS(=O)(=O)c3c(F)cccc3F)c2F)c(-c2ccnc(N)n2)s1]

or a pharmaceutically acceptable salt thereof; and
the Compound A is a compound of structure (I):

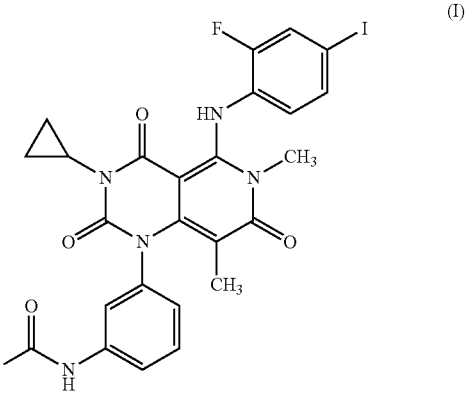

or a pharmaceutically acceptable salt or solvate thereof.

In some embodiments of any of the above aspects of the invention, the PD-1 antagonist in the combination is an anti-human PD-1 antibody or an antigen binding fragment thereof, and the combination is for use in the treatment of a cancer in a human. In more preferred embodiments, the cancer is melanoma.

In other embodiments of any of the above aspects of the invention, the combination comprises each of Compound A and Compound B, the PD-1 antagonist is an anti-human PD-1 antibody or an antigen binding fragment thereof, and the combination is for use in treating a human with advanced or metastatic melanoma that tests positive for a BRAF V600 mutation.

In still other embodiments of any of the above aspects of the invention, the combination does not comprise Compound B, the PD-1 antagonist is an anti-PD-1 antibody or an antigen binding fragment thereof, and the combination is for use in treating patients with advanced or metastatic melanoma that tests negative for a BRAF V600 mutation.

In yet other embodiments of any of the above aspects of the invention, the combination does not comprise Compound A, the PD-1 antagonist is an anti-human PD-1 antibody or an antigen binding fragment thereof, and the combination is for use in treating a human with advanced or metastatic melanoma that tests positive for a BRAF V600 mutation.

In another aspect of the present invention, there is provided a pharmaceutical composition for use in combination with a PD-1 antagonist for treating a cancer, wherein the pharmaceutical composition comprises a Compound A and/or a Compound B together with a pharmaceutically acceptable diluent or carrier, and wherein the Compound A is a compound of structure (I):

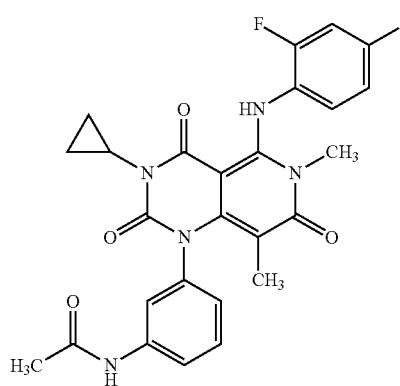

or a pharmaceutically acceptable salt or solvate thereof; and the compound B is a compound of structure (II):

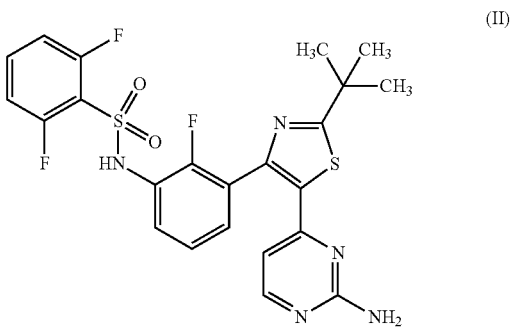 [SMILES: CC(C)(C)c1nc(-c2cccc(NS(=O)(=O)c3c(F)cccc3F)c2F)c(-c2ccnc(N)n2)s1]

or a pharmaceutically acceptable salt thereof.

In some embodiments, the pharmaceutical composition of the invention comprises each of Compound A and Compound B, the PD-1 antagonist is an anti-human PD-1 antibody or an antigen binding fragment thereof, and the cancer is advanced melanoma that tests positive for a BRAF V600 mutation.

In other embodiments, the pharmaceutical composition of the invention does not comprise Compound B, the PD-1 antagonist is an anti-human PD-1 antibody or an antigen binding fragment thereof, and the cancer is advanced melanoma that tests negative for a BRAF V600 mutation.

In yet other embodiments, the above pharmaceutical composition of the invention does not comprise Compound A, the PD-1 antagonist is an anti-human PD-1 antibody or an antigen binding fragment thereof, and the cancer is advanced melanoma that tests positive for a BRAF V600 mutation.

In yet another aspect of the present invention, there is provided a pharmaceutical composition comprising a PD-1 antagonist together with a pharmaceutically acceptable diluent or carrier for use in a combination therapy for treating a cancer, wherein the combination therapy comprises the pharmaceutical composition and one or both of a Compound A and a Compound B, wherein the Compound A is a compound of structure (I):

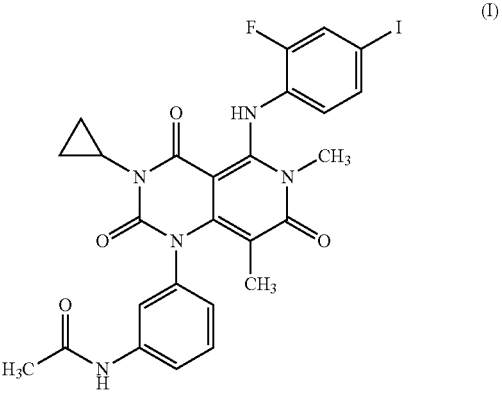 [SMILES: CC(=O)Nc1cccc(-n2c(=O)n(C3CC3)c(=O)c3c(Nc4ccc(I)cc4F)n(C)c(=O)c(C)c32)c1]

or a pharmaceutically acceptable salt or solvate thereof; and wherein the Compound B is a compound of structure (II):

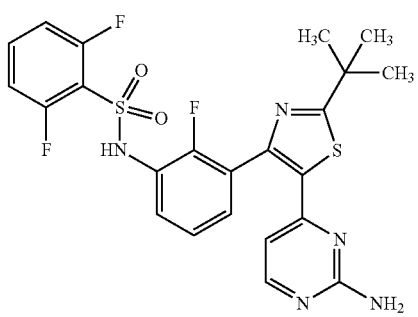

(II)

or a pharmaceutically acceptable salt thereof.

In some embodiments, the PD-1 antagonist in a pharmaceutical composition of the invention is an anti-human PD-1 antibody or an antigen binding fragment thereof.

In another aspect there is provided the use of a combination comprising MK-3475 or an antigen binding fragment thereof and one or both of a Compound A and a Compound B in the manufacture of medicaments for use in combination for the treatment of cancer, wherein:
the Compound B is a compound of structure (II)

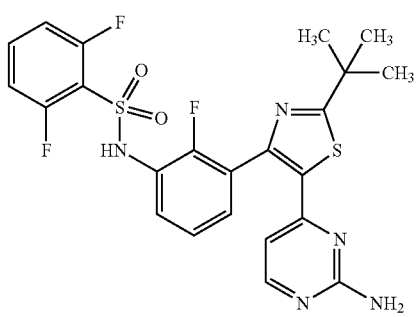

(II)

or a pharmaceutically acceptable salt thereof; and
the Compound A is a compound of structure (I)

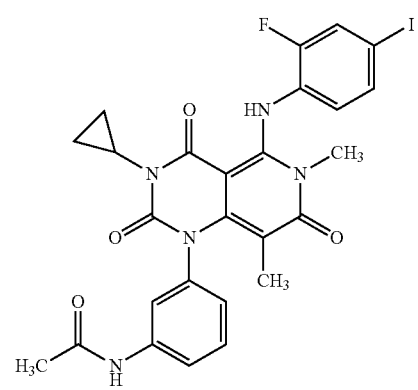

(I)

or a pharmaceutically acceptable salt or solvate thereof.

In another aspect, there is provided a method of treating cancer in a mammal comprising administering to said mammal a combination therapy, wherein the combination therapy comprises a therapeutically effective amount of a PD-1 antagonist and one or both of a therapeutically effective amount of a Compound A and a therapeutically effective amount of a Compound B, wherein:
the Compound B is a compound of structure (II):

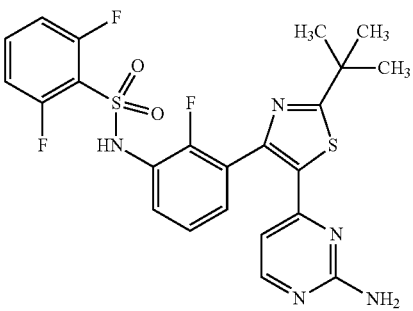

(II)

or a pharmaceutically acceptable salt thereof; and
the Compound A is a compound of structure (I):

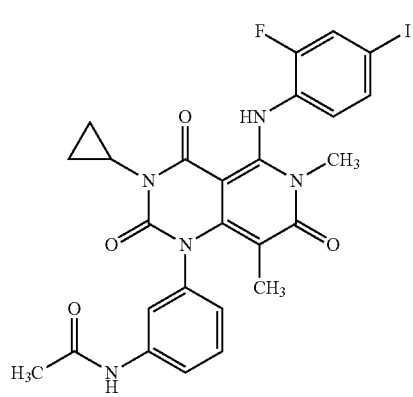

(I)

or a pharmaceutically acceptable salt or solvate thereof.

In another aspect, there is provided a method of treating cancer in a human in need thereof comprising administering to the human a combination therapy, wherein the combination therapy comprises a therapeutically effective amount of a PD-1 antagonist and one or both of a therapeutically effective amount of a Compound A and a therapeutically effective amount of a Compound B, wherein the PD-1 antagonist is an anti-human PD-1 antibody or an antigen binding fragment thereof, the Compound B is N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof and the Compound A is N-{3-[3-cyclopropyl-5-(2-fluoro-4-iodo-phenylamino) 6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate thereof.

In another aspect, there is provided a method of treating cancer in a human in need thereof comprising administering to the human a therapeutically effective amount of a combination therapy comprising a PD-1 antagonist and one or both of a Compound A and a Compound B, wherein the PD-1 antagonist is an anti-human PD-1 antibody or an antigen binding fragment, Compound B is N-{3-[5-(2-Amino-4-pyrimidinyl)-2-(1,1-dimethylethyl)-1,3-thiazol-4- yl]-2-fluorophenyl}-2,6-difluorobenzenesulfonamide methanesulfonate, and the Compound A is N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide dimethyl sulfoxide solvate.

In a further aspect of the invention is provided a method of treating cancer in a mammal in need thereof which comprises administering a therapeutically effective amount of a combination of the invention wherein the combination is administered within a specific period and for a duration of time.

In some embodiments, a treatment method of the invention comprises treating a human diagnosed with advanced melanoma that tests positive for a BRAF V600 mutation and the administered combination therapy comprises each of Compound A and Compound B, and an anti-human PD-1 antibody.

In some embodiments, a treatment method of the invention comprises treating a human diagnosed with advanced melanoma that tests negative for a BRAF V600 mutation, and the administered combination therapy comprises each of Compound A and an anti-human PD-1 monoclonal antibody as the PD-1 antagonist, but does not comprise Compound B.

In yet other embodiments, a human diagnosed with advanced melanoma that tests positive for a BRAF V600 mutation is treated by administering a combination therapy that comprises each of an anti-human PD-1 monoclonal antibody as the PD-1 antagonist and Compound B, but does not comprise Compound A.

In some embodiments of any of the above aspects of the invention, the cancer tests positive for human PD-L1 expression, the PD-1 antagonist is nivolumab or MK-3475, and in particularly preferred embodiments, the PD-1 antagonist is MK-3475, Compound A is trametinib and Compound B is dabrafenib.

BRIEF DESCRIPTION OF THE DRAWINGS

FIG. 1 shows amino acid sequences of the light chain and heavy chain CDRs for an exemplary anti-PD-1 monoclonal antibody useful in the present invention (SEQ ID NOs:1-6).

FIG. 2 shows amino acid sequences of the light chain and heavy chain CDRs for another exemplary anti-PD-1 monoclonal antibody useful in the present invention (SEQ ID NOs:7-12).

FIG. 3 shows amino acid sequences of the heavy chain variable region and full length heavy chain for an exemplary anti-PD-1 monoclonal antibody useful in the present invention (SEQ ID NO:13 and SEQ ID NO:14).

FIG. 4 shows amino acid sequences of alternative light chain variable regions for an exemplary anti-PD-1 monoclonal antibody useful in the present invention (SEQ ID NOs:15-17).

FIG. 5 shows amino acid sequences of alternative light chains for an exemplary anti-PD-1 monoclonal antibody useful in the present invention. FIG. 5A shows the amino acid sequences of alternative light chains, K09A-L-11 and K09A-L-16 (SEQ ID NOs: 18 and 19, respectively). FIG. 5B shows the amino acid sequence of alternative light chain, K09A-L-17 (SEQ ID NO: 20).

FIG. 6 shows amino acid sequences of the heavy and light chains for MK-3475 (SEQ ID NOs. 21 and 22, respectively).

FIG. 7 shows amino acid sequences of the heavy and light chains for nivolumab (SEQ ID NOs. 23 and 24, respectively).

DETAILED DESCRIPTION OF THE INVENTION

I. Abbreviations

Figure 8A:
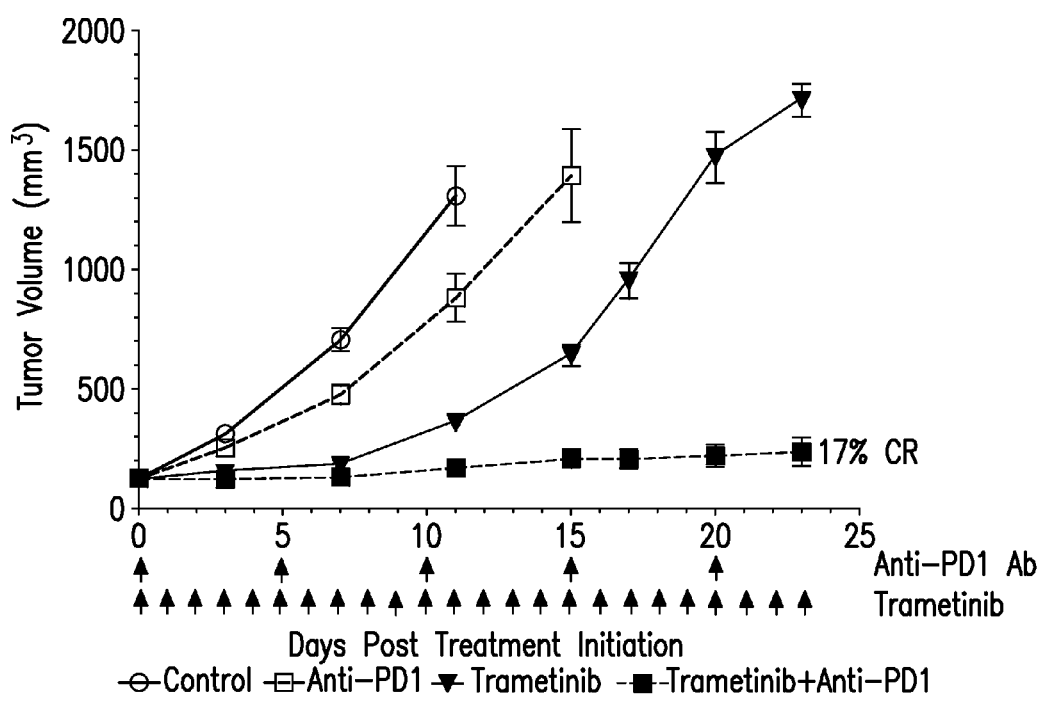
FIG. 8 compares the anti-tumor effect in tumor-bearing mice of combination therapy with a murine anti-mouse PD-1 antibody and trametinib versus monotherapy with either agent alone, with FIG. 8A showing the mean tumor volume at various days during treatment with an isotype antibody+vehicle (Control), the murine anti-PD-1 Ab (Anti-PD-1), trametinib, or concurrent administration of both trametinib and Anti-PD-1, and FIG. 8B showing the tumor volume values for individual mice in each treatment group on the first day of treatment (left graph, Day 0) or after 23 days of treatment (right graph, Day 23).

Throughout the detailed description and examples of the invention the following abbreviations will be used:
BID One dose twice a day
CDR Complementarity determining region
CHO Chinese hamster ovary
DFS Disease free survival
DTR Dose limiting toxicity
FFPE Formalin-fixed, paraffin-embedded
FR Framework region
IgG Immunoglobulin G
IHC Immunohistochemistry or immunohistochemical
MTD Maximum Tolerated Dose
NCBI National Center for Biotechnology Information
NCI National Cancer Institute
OR Overall Response
OS Overall Survival
PD Progressive Disease
PFS Progression Free Survival
PR Partial Response
Q2W One dose every two weeks
Q3W One dose every three weeks
QD One dose per day
RECIST Response Evaluation Criteria in Solid Tumors
SD Stable Disease
VH Immunoglobulin heavy chain variable region
VK Immunoglobulin kappa light chain variable region II. Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic.

In general, the basic monoclonal antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence. An antibody that specifically binds to a specified human target protein preferably refers to an antibody that binds to that target protein with a $K_D$ of $1\times10^{-7\,M}$ or less, more preferably $5\times10^{-8\,M}$ or less, more preferably $1\times10^{-8\,M}$ or less, more preferably $5\times10^{-9\,M}$ or less. A preferred method for determining the $K_D$ of an antibody is by using surface plasmon resonance.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

As used herein, the B-Raf inhibitor N-{3-[5-(2-Amino-4-pyrimidinyl)-2-(1,1-dimethylethyl)-1,3-thiazol-4-yl]-2-fluorophenyl}-2,6-difluorobenzenesulfonamide or pharmaceutically acceptable salt thereof, is represented by a compound structure (II):

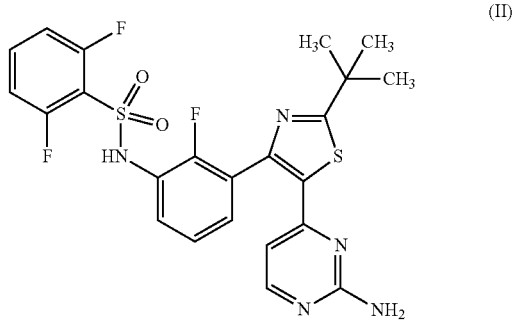 [SMILES: CC(C)(C)c1nc(-c2cccc(NS(=O)(=O)c3c(F)cccc3F)c2F)c(-c2ccnc(N)n2)s1]

(II)

or a pharmaceutically acceptable salt thereof. For convenience, the group of possible compound and salts is collectively referred to as Compound B, meaning that reference to Compound B will refer to any of the compound or pharmaceutically acceptable salt thereof in the alternative. A particularly preferred B-Raf inhibitor for use in any of the aspects of the invention is dabrafenib mesylate, which is known by the trade name TAFINLAR®. TAFINLAR (dabrafenib) capsules are supplied as 50-mg and 75-mg capsules for oral administration, and contain the following inactive ingredients: colloidal silicon dioxide, magnesium stearate, and microcrystalline cellulose.

The term BRAF V600 mutation means a substitution of glutamate (E) for valine at position 600 (V600E) and/or a substitution of lysine (K) for valine at position 600 (V600K). A positive test for a BRAF V600 mutation means the detection of the presence of either or both of these substitutions, and a negative test for a BRAF V600 mutation means the absence of both of these substitutions. A commercially available in vitro diagnostics (IVD) kit for detecting BRAF V600E and V600K mutations is marketed by bioMérieux SA under the tradename the THxID™ BRAF.

"Biotherapeutic agent" means a biological molecule, such as an antibody or fusion protein, that blocks ligand/receptor signaling in any biological pathway that supports tumor maintenance and/or growth or suppresses the anti-tumor immune response.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Particularly preferred cancers that may be treated in accordance with the present invention have a positive test for expression of PD-L1 and either a positive test for a BRAF V600 mutation (for embodiments that include a Compound B) or a negative test for a BRAF V600 mutation (for embodiments that do not include a Compound B). As used herein, advanced melanoma refers to unresectable Stage III) and metastatic melanoma refers to Stage IV melanoma.

"CDR" or "CDRs" as used herein means complementarity determining region(s) in a immunoglobulin variable region, defined using the Kabat numbering system, unless otherwise indicated.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytoxic/antitumor antibiotics, topisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, anti-sense oligonucleotides that that inhibit expression of genes implicated in abnormal cell proliferation or tumor growth. Chemotherapeutic agents useful in the treatment methods of the present invention include cytostatic and/or cytotoxic agents.

"Chothia" as used herein means an antibody numbering system described in Al-Lazikani et al., *JMB* 273:927-948 (1997).

"Combination of the invention" and "combination therapy of the invention" refers to a combination of a PD-1 antagonist and one or both of a BRAF inhibitor, suitably Compound B, and a MEK inhibitor, suitably Compound A.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |

TABLE 1-continued

Exemplary Conservative Amino Acid Substitutions

| Original residue | Conservative substitution |
|---|---|
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a PD-1 antagonist that consists essentially of a recited amino acid sequence may also include one or more amino acids, including substitutions of one or more amino acid residues, which do not materially affect the properties of the binding compound.

"Diagnostic anti-PD-L monoclonal antibody" means a mAb which specifically binds to the mature form of the designated PD-L (PD-L1 or PDL2) that is expressed on the surface of certain mammalian cells. A mature PD-L lacks the presecretory leader sequence, also referred to as leader peptide The terms "PD-L" and "mature PD-L" are used interchangeably herein, and shall be understood to mean the same molecule unless otherwise indicated or readily apparent from the context.

As used herein, a diagnostic anti-human PD-L1 mAb refers to a monoclonal antibody that specifically binds to mature human PD-L1. A mature human PD-L1 molecule consists of amino acids 19-290 of the following sequence:

```
                                              (SEQ ID NO: 25)
MRIFAVFIFMTYWHLLNAFTVTVPKDLYVVEYGSNMTIECKFPVEKQLD

LAALIVYWEMEDKNIIQFVHGEEDLKVQHSSYRQRARLLKDQLSLGNAA

LQITDVKLQDAGVYRCMISYGGADYKRITVKVNAPYNKINQRILVVDPV

TSEHELTCQAEGYPKAEVIWTSSDHQVLSGKTTTTNSKREEKLFNVTST

LRINTTTNEIFYCTFRRLDPEENHTAELVIPELPLAHPPNERTHLVILG

AILLCLGVALTFIFRLRKGRMMDVKKCGIQDTNSKKQSDTHLEET.
```

Specific examples of diagnostic anti-human PD-L1 mAbs useful as diagnostic mAbs for immunohistochemistry (IHC) detection of PD-L1 expression in formalin-fixed, paraffin-embedded (FFPE) tumor tissue sections are antibody 20C3 and antibody 22C3, which are described in the copending international patent application PCT/US13/075932, filed 18 Dec. 2013. Another anti-human PD-L1 mAb that has been reported to be useful for IHC detection of PD-L1 expression in FFPE tissue sections (Chen, B. J. et al., Clin Cancer Res 19: 3462-3473 (2013)) is a rabbit anti-human PD-L1 mAb publicly available from Sino Biological, Inc. (Beijing, P.R. China; Catalog number 10084-R015).

"Framework region" or "FR" as used herein means the immunoglobulin variable regions excluding the CDR regions.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared ×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

As used herein, the MEK inhibitor N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate thereof, is represented by a compound of structure (I):

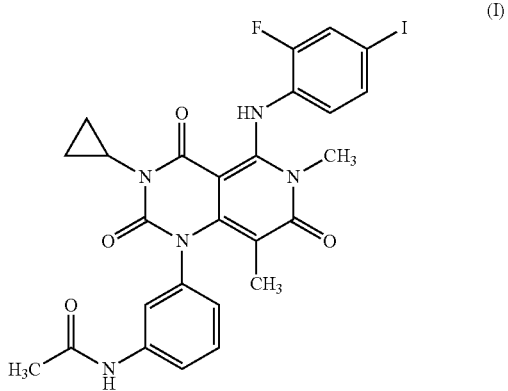 [SMILES: CC(=O)Nc1cccc(-n2c(=O)n(C3CC3)c(=O)c3c(Nc4ccc(I)cc4F)n(C)c(=O)c(C)c32)c1]

or pharmaceutically acceptable salt or solvate thereof. For convenience, the group of possible compound and salts or solvates is collectively referred to as Compound A, meaning that reference to Compound A will refer to any of the compound or pharmaceutically acceptable salt or solvate thereof in the alternative. Depending on naming convention, the compound of formula (I) may also properly be referred to as N-{3-[3-cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl]phenyl}acetamide. A particularly preferred MEK inhibitor for use in any of the aspects of the invention is trametinib dimethyl sulfoxide, which is known by the trade name MEKINIST™. MEKINIST (trametinib) tablets are supplied as 0.5-mg, 1-mg and 2-mg tablets for oral administration. The core of MEKINIST tablets contain the inactive ingredients of colloidal silicon dioxide, croscarmellose sodium, hypromellse, magnesium stearate (vegetable source) mannitol, microcrystalline cellulose, sodium and lauryl sulfate, and the coating of MEKINIST tablets contain the inactive ingredients of hypromellose, iron oxide red (2-mg tablets), iron oxide yellow (0.5-mg tablets), polyethylene glycol, polysorbate 80 (2-mg tablets) and titanium dioxide.

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

"Patient" or "subject" refers to any single subject for which therapy is desired or that is participating in a clinical trial, epidemiological study or used as a control, including humans and mammalian veterinary patients such as cattle, horses, dogs, and cats.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any embodiments of the aspects or embodiments of the present invention in which a human individual is to be treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the various aspects and embodiments of the present invention, are described in U.S. Pat. No. 7,488,802, U.S. Pat. No. 7,521,051, U.S. Pat. No. 8,008,449, U.S. Pat. No. 8,354,509, U.S. Pat. No. 8,168,757, WO2004/004771, WO2004/072286, WO2004/056875, and US2011/0271358.

Specific anti-human PD-1 mAbs useful as the PD-1 antagonist in any of the aspects and embodiments of the present invention include: MK-3475, a humanized IgG4 mAb with the structure described in *WHO Drug Information*, Vol. 27, No. 2, pages 161-162 (2013) and which comprises the heavy and light chain amino acid sequences shown in FIG. 6; nivolumab, a human IgG4 mAb with the structure described in *WHO Drug Information*, Vol. 27, No. 1, pages 68-69 (2013) and which comprises the heavy and light chain amino acid sequences shown in FIG. 7; the humanized antibodies h409A11, h409A16 and h409A17, which are described in WO2008/156712, and AMP-514, which is being developed by Medimmune.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

In some preferred embodiments of any of the aspects of the present invention, the PD-1 antagonist is a monoclonal antibody, or antigen binding fragment thereof, which binds to human PD-1 and comprises: (a) light chain CDRs SEQ ID NOs: 1, 2 and 3 and heavy chain CDRs SEQ ID NOs: 4, 5 and 6; or (b) light chain CDRs SEQ ID NOs: 7, 8 and 9 and heavy chain CDRs SEQ ID NOs: 10, 11 and 12.

In other preferred embodiments of any of the aspects of the present invention, the PD-1 antagonist is a monoclonal antibody, or antigen binding fragment thereof, which specifically binds to human PD-1 and comprises (a) a heavy chain variable region comprising SEQ ID NO:13 or a variant thereof, and (b) a light chain variable region comprising an amino acid sequence selected from the group consisting of SEQ ID NO:15 or a variant thereof; SEQ ID NO:16 or a variant thereof; and SEQ ID NO: 17 or a variant thereof. A variant of a heavy chain variable region sequence is identical to the reference sequence except having up to 17 conservative amino acid substitutions in the framework region (i.e., outside of the CDRs), and preferably has less than ten, nine, eight, seven, six or five conservative amino acid substitutions in the framework region. A variant of a light chain variable region sequence is identical to the reference sequence except having up to five conservative amino acid substitutions in the framework region (i.e., outside of the CDRs), and preferably has less than four, three or two conservative amino acid substitution in the framework region.

In another preferred embodiment of the aspects of the present invention, the PD-1 antagonist is a monoclonal antibody which specifically binds to human PD-1 and comprises (a) a heavy chain comprising SEQ ID NO: 14 and (b) a light chain comprising SEQ ID NO:18, SEQ ID NO:19 or SEQ ID NO:20.

In yet another preferred embodiment of the aspects of the present invention, the PD-1 antagonist is a monoclonal antibody which specifically binds to human PD-1 and comprises (a) a heavy chain comprising SEQ ID NO: 14 and (b) a light chain comprising SEQ ID NO:18.

Table 2 below provides a list of the amino acid sequences of exemplary anti-PD-1 mAbs for use in the various aspects of the present invention, and the sequences are shown in FIGS. 1-5.

TABLE 2

| Exemplary anti-human PD-1 antibodies | |
|---|---|
| A. Comprises light and heavy chain CDRs of hPD-1.08A in WO2008/156712 | |
| CDRL1 | SEQ ID NO: 1 |
| CDRL2 | SEQ ID NO: 2 |
| CDRL3 | SEQ ID NO: 3 |
| CDRH1 | SEQ ID NO: 4 |
| CDRH2 | SEQ ID NO: 5 |
| CDRH3 | SEQ ID NO: 6 |
| B. Comprises light and heavy chain CDRs of hPD-1.09A in WO2008/156712 | |
| CDRL1 | SEQ ID NO: 7 |
| CDRL2 | SEQ ID NO: 8 |
| CDRL3 | SEQ ID NO: 9 |
| CDRH1 | SEQ ID NO: 10 |
| CDRH2 | SEQ ID NO: 11 |
| CDRH3 | SEQ ID NO: 12 |
| C. Comprises the mature h109A heavy chain variable region and one of the mature K09A light chain variable regions in WO2008/156712 | |
| Heavy chain VR | SEQ ID NO: 13 |
| Light chain VR | SEQ ID NO: 15 or |
|  | SEQ ID NO: 16 or |
|  | SEQ ID NO: 17 |
| D. Comprises the mature 409 heavy chain and one of the mature K09A light chains in WO2008/156712 | |
| Heavy chain | SEQ ID NO: 14 |
| Light chain | SEQ ID NO: 18 or |
|  | SEQ ID NO: 19 or |
|  | SEQ ID NO: 20 |

"PD-L1" or "PD-L2" expression as used herein means any detectable level of expression of the designated PD-L protein on the cell surface or of the designated PD-L mRNA within a cell or tissue. PD-L protein expression may be detected with a diagnostic PD-L antibody in an IHC assay of a tumor tissue section or by flow cytometry. Alternatively, PD-L protein expression by tumor cells may be detected by PET imaging, using a binding agent (e.g., antibody fragment, affibody and the like) that specifically binds to the desired PD-L target, e.g., PD-L1 or PD-L2. Techniques for detecting and measuring PD-L mRNA expression include RT-PCR and realtime quantitative RT-PCR.

Several approaches have been described for quantifying PD-L1 protein expression in IHC assays of tumor tissue sections. See, e.g., Thompson, R. H., et al., *PNAS* 101 (49); 17174-17179 (2004); Thompson, R. H. et al., *Cancer Res.* 66:3381-3385 (2006); Gadiot, J., et al., *Cancer* 117:2192-2201 (2011); Taube, J. M. et al., *Sci Transl Med* 4, 127ra37 (2012); and Toplian, S. L. et al., *New Eng. J Med.* 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression is at least 1%, and preferably 5% of total tumor cells.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is 5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is 5.

The level of PD-L mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue. In some preferred embodiments, PD-L1 expression in a tumor sample is determined to be elevated if PD-L1 protein (and/or PD-L1 mRNA) in the sample is at least 10%, 20%, or 30% greater than in the control.

"RECIST 1.1 Response Criteria" as used herein means the definitions set forth in Eisenhauer et al., E. A. et al., *Eur. J Cancer* 45:228-247 (2009) for target lesions or nontarget lesions, as appropriate based on the context in which response is being measured.

"Sustained response" means a sustained therapeutic effect after cessation of treatment with a therapeutic agent, or a combination therapy described herein. In some embodiments, the sustained response has a duration that is at least the same as the treatment duration, or at least 1.5, 2.0, 2.5 or 3 times longer than the treatment duration.

"Tissue Section" refers to a single part or piece of a tissue sample, e.g., a thin slice of tissue cut from a sample of a normal tissue or of a tumor.

"Treat" or "treating" a cancer as used herein means to administer a combination of the invention to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, *J. Nucl. Med.* 50:1S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some embodiments, the treatment achieved by a combination of the invention is any of PR, CR, OR, PFS, DFS and OS. PFS, also referred to as "Time to Tumor Progression" indicates the length of time during and after treatment that the cancer does not grow, and includes the amount of time patients have experienced a CR or PR, as well as the amount of time patients have experienced SD. DFS refers to the length of time during and after treatment that the patient remains free of disease. OS refers to a prolongation in life expectancy as compared to naive or untreated individuals or patients. In some preferred embodiments, response to a combination of the invention is any of PR, CR, PFS, DFS, OR or OS that is assessed using RECIST 1.1 response criteria. The treatment regimen for a combination of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

The terms "treatment regimen", "dosing protocol" and dosing regimen are used interchangeably to refer to the dose and timing of administration of each therapeutic agent in a combination of the invention.

"Tumor" or "neoplasm" as applied to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Variable regions" or "V region" as used herein means the segment of IgG chains which is variable in sequence between different antibodies. It extends to Kabat residue 109 in the light chain and 113 in the heavy chain.

III. Combinations, Compositions, Uses and Treatment Methods

The administration of a therapeutically effective amount of the combinations of the invention are advantageous over the individual component compounds in that the combinations provide one or more of the following improved properties when compared to the individual administration of a therapeutically effective amount of a component compound: i) a greater anticancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, or vi) an increase in the bioavailability of one or both of the component compounds.

Compounds A and/or B may contain one or more chiral atoms, or may otherwise be capable of existing as enantiomers. Accordingly, the compounds of this invention include mixtures of enantiomers as well as purified enantiomers or enantiomerically enriched mixtures. Also, it is understood that all tautomers and mixtures of tautomers are included within the scope of Compound A and Compound B.

Also, it is understood that compounds A and B may be presented, separately or both, as solvates. As used herein, the term "solvate" refers to a complex of variable stoichiometry formed by a solute (in this invention, compounds of formula (I) or (II) or a salt thereof and a solvent. Such solvents for the purpose of the invention may not interfere with the biological activity of the solute. Examples of suitable solvents include, but are not limited to, water, methanol, dimethyl sulfoxide, ethanol and acetic acid. In one embodiment, the solvent used is a pharmaceutically acceptable solvent. In another embodiment, the solvent used is water.

Compounds A and B may have the ability to crystallize in more than one form, a characteristic, which is known polymorphism, and it is understood that such polymorphic forms ("polymorphs") are within the scope of Compounds A and B. Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

Compound A is disclosed and claimed, along with pharmaceutically acceptable salts and solvates thereof, as being useful as an inhibitor of MEK activity, particularly in treatment of cancer, in International Application No. PCT/JP2005/011082, having an International filing date of Jun. 10, 2005; International Publication Number WO 2005/121142 and an International Publication date of Dec. 22, 2005, the entire disclosure of which is hereby incorporated by reference, Compound A is the compound of Example 4-1. Compound A can be prepared as described in International Application No. PCT/JP2005/011082. Compound A can be prepared as described in United States Patent Publication No. US 2006/0014768, published Jan. 19, 2006, the entire disclosure of which is hereby incorporated by reference.

Suitably, Compound A is in the form of a dimethyl sulfoxide solvate. Suitably, Compound A is in the form of a sodium salt. Suitably, Compound A is in the form of a solvate selected from: hydrate, acetic acid, ethanol, nitromethane, chlorobenzene, 1-pentanci, isopropyl alcohol, ethylene glycol and 3-methyl-1-butanol. These solvates and salt forms can be prepared by one of skill in the art from the description in International Application No. PCT/JP2005/011082 or United States Patent Publication No. US 2006/0014768.

Compound B is disclosed and claimed, along with pharmaceutically acceptable salts thereof, as being useful as an inhibitor of BRaf activity, particularly in the treatment of cancer, in PCT patent application PCT/US09/42682. Compound B is embodied by Examples 58a through 58e of the application. The PCT application was published on 12 Nov. 2009 as publication WO2009/137391, and is hereby incorporated by reference.

More particularly, Compound B may be prepared according to the methods below:

Method 1: Compound B (First Crystal Form)—N-{3-[5-(2-Amino-4-pyrimidinyl)-2-(1,1-dimethylethyl)-1,3-thiazol-4-yl]-2-fluorophenyl}-2,6-difluorobenzenesulfonamide

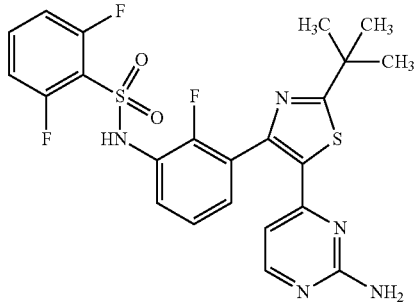 [SMILES: CC(C)(C)c1nc(-c2cccc(NS(=O)(=O)c3c(F)cccc3F)c2F)c(-c2ccnc(N)n2)s1]

A suspension of N-{3-[5-(2-chloro-4-pyrimidinyl)-2-(1,1-dimethylethyl)-1,3-thiazol-4-yl]-2-fluorophenyl}-2,6-difluorobenzenesulfonamide (196 mg, 0.364 mmol) and ammonia in methanol 7M (8 ml, 56.0 mmol) was heated in a sealed tube to 90° C. for 24 h. The reaction was diluted with DCM and added silica gel and concentrated. The crude product was chromatographed on silica gel eluting with 100% DCM to 1:1 [DCM:(9:1 EtOAc:MeOH)]. The clean fractions were concentrated to yield the crude product. The crude product was repurified by reverse phase HPLC (a gradient of acetonitrile:water with 0.1% TFA in both). The combined clean fractions were concentrated then partitioned between DCM and saturated NaHCO$_3$. The DCM layer was separated and dried over Na$_2$SO$_4$. The title compound, N-{3-[5-(2-amino-4-pyrimidinyl)-2-(1,1-dimethylethyl)-1,3-thiazol-4-yl]-2-fluorophenyl}-2,6-difluorobenzenesulfonamide was obtained (94 mg, 47% yield). $^1$H NMR (400 MHz, DMSO-d6) δ ppm 10.83 (s, 1H), 7.93 (d, J=5.2 Hz, 1H), 7.55-7.70 (m, 1H), 7.35-7.43 (m, 1H), 7.31 (t, J=6.3 Hz, 1H), 7.14-7.27 (m, 3H), 6.70 (s, 2H), 5.79 (d, J=5.13 Hz, 1H), 1.35 (s, 9H). MS (ESI): 519.9 [M+H]$^+$.

Method 2: Compound B (alternative crystal form)—N-{3-[5-(2-Amino-4-pyrimidinyl)-2-(1,1-dimethylethyl)-1,3-thiazol-4-yl]-2-fluorophenyl}-2,6-difluorobenzenesulfonamide 19.6 mg of N-{3-[5-(2-Amino-4-pyrimidinyl)-2-(1,1-dimethylethyl)-1,3-thiazol-4-yl]-2-fluorophenyl}-2,6-difluorobenzenesulfonamide (may be prepared in accordance with example 58a) was combined with 500 L of ethyl acetate in a 2-mL vial at room temperature. The slurry was temperature-cycled between 0-40° C. for 48 hrs. The resulting slurry was allowed to cool to room temperature and the solids were collected by vacuum filtration. The solids were analyzed by Raman, PXRD, DSC/TGA analyses, which indicated a crystal form different from the crystal form resulting from Example 58a, above.

Method 3: Compound B (Alternative Crystal Form, Large Batch)—N-{3-[5-(2-amino-4-pyrimidinyl)-2-(1,1-dimethylethyl)-1,3-thiazol-4-yl]-2-fluorophenyl}-2,6-difluorobenzenesulfonamide

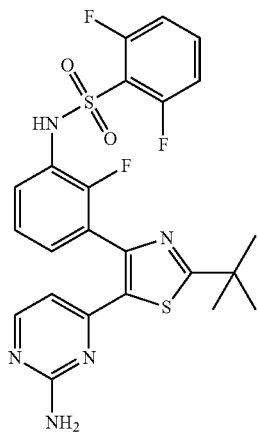 [SMILES: CC(C)(C)c1nc(-c2cccc(NS(=O)(=O)c3c(F)cccc3F)c2F)c(-c2ccnc(N)n2)s1]

Step A: methyl 3-{[(2,6-difluorophenyl)sulfonyl]amino}-2-fluorobenzoate

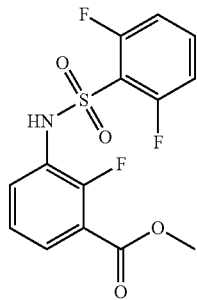 [SMILES: COC(=O)c1cccc(NS(=O)(=O)c2c(F)cccc2F)c1F]

Methyl 3-amino-2-fluorobenzoate (50 g, 1 eq) was charged to reactor followed by dichloromethane (250 mL, 5 vol). The contents were stirred and cooled to ~15° C. and pyridine (26.2 mL, 1.1 eq) was added. After addition of the pyridine, the reactor contents were adjusted to ~15° C. and the addition of 2,6-diflurorobenzenesulfonyl chloride (39.7 mL, 1.0 eq) was started via addition funnel. The temperature during addition was kept <25° C. After complete addition, the reactor contents were warmed to 20-25° C. and held overnight. Ethyl acetate (150 mL) was added and dichloromethane was removed by distillation. Once distillation was complete, the reaction mixture was then diluted once more with ethyl acetate (5 vol) and concentrated. The reaction mixture was diluted with ethyl acetate (10 vol) and water (4 vol) and the contents heated to 50-55° C. with stirring until all solids dissolve. The layers were settled and separated. The organic layer was diluted with water (4 vol) and the contents heated to 50-55° for 20-30 min. The layers were settled and then separated and the ethyl acetate layer was evaporated under reduced pressure to ~3 volumes. Ethyl Acetate (5 vol.) was added and again evaporated under reduced pressure to ~3 volumes. Cyclohexane (9 vol) was then added to the reactor and the contents were heated to reflux for 30 min then cooled to 0° C. The solids were filtered and rinsed with cyclohexane (2×100 mL). The solids were air dried overnight to obtain methyl 3-{[(2,6-difluorophenyl)sulfonyl]amino}-2-fluorobenzoate (94.1 g, 91%).

Step B: N-{3-[(2-chloro-4-pyrimidinyl)acetyl]-2-fluorophenyl}-2,6-difluorobenzenesulfonamide

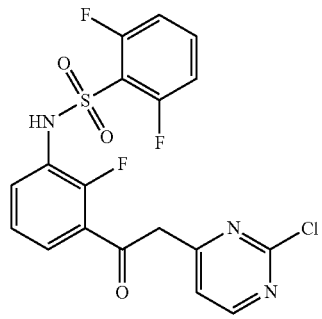 [SMILES: O=C(Cc1ccnc(Cl)n1)c1cccc(NS(=O)(=O)c2c(F)cccc2F)c1F]

Methyl 3-{[(2,6-difluorophenyl)sulfonyl]amino}-2-fluorobenzoate (490 g, 1 equiv.), prepared generally in accordance with Step A, above, was dissolved in THF (2.45 L, 5 vols) and stirred and cooled to 0-3° C. 1M lithium bis(trimethylsilyl)amide in THF (5.25 L, 3.7 equiv.) solution was charged to the reaction mixture followed addition of 2-chloro-4-methylpyrimidine (238 g, 1.3 equiv.) in THF (2.45 L, 5 vols). The reaction was then stirred for 1 hr. The reaction was quenched with 4.5M HCl (3.92 L, 8 vols). The aqueous layer (bottom layer) was removed and discarded. The organic layer was concentrated under reduced pressure to ~2 L. IPAC (isopropyl acetate) (2.45 L) was added to the reaction mixture which was then concentrated to ~2 L. IPAC (0.5 L) and MTBE (2.45 L) was added and stirred overnight under $N_2$. The solids were filtered. The solids and mother filtrate added back together and stirred for several hours. The solids were filtered and washed with MTBE (~5 vol). The solids were placed in vacuum oven at 50° C. overnight. The solids were dried in vacuum oven at 30° C. over weekend to obtain N-{3-[(2-chloro-4-pyrimidinyl)acetyl]-2-fluorophenyl}-2,6-difluorobenzenesulfonamide (479 g, 72%).

Step C: N-{3-[5-(2-chloro-4-pyrimidinyl)-2-(1,1-dimethylethyl)-1,3-thiazol-4-yl]-2-fluorophenyl}-2,6-difluorobenzenesulfonamide

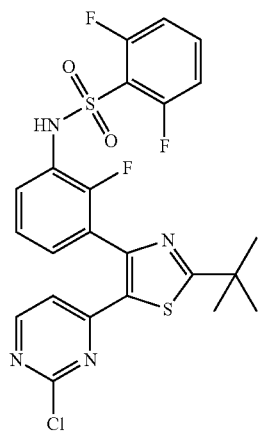 [SMILES: CC(C)(C)c1nc(-c2cccc(NS(=O)(=O)c3c(F)cccc3F)c2F)c(-c2ccnc(Cl)n2)s1]

To a reactor vessel was charged N-{3-[(2-chloro-4-pyrimidinyl)acetyl]-2-fluorophenyl}-2,6-difluorobenzenesulfonamide (30 g, 1 eq) followed by dichloromethane (300 mL). The reaction slurry was cooled to ~10° C. and N-bromosuccinimide ("NBS") (12.09 g, 1 eq) was added in 3 approximately equal portions, stirring for 10-15 minutes between each addition. After the final addition of NBS, the reaction mixture was warmed to ~20° C. and stirred for 45 min. Water (5 vol) was then added to the reaction vessel and the mixture was stirred and then the layers separated. Water (5 vol) was again added to the dichloromethane layer and the mixture was stirred and the layers separated. The dichloromethane layers were concentrated to ~120 mL. Ethyl acetate (7 vol) was added to the reaction mixture and concentrated to ~120 mL. Dimethylacetamide (270 mL) was then added to the reaction mixture and cooled to ~10° C. 2,2-Dimethylpropanethioamide (1.3 g, 0.5 eq) in 2 equal portions was added to the reactor contents with stirring for ~5 minutes between additions. The reaction was warmed to 20-25° C. After 45 min, the vessel contents were heated to 75° C. and held for 1.75 hours. The reaction mixture was then cooled to 5° C. and water (270 ml) was slowly charged keeping the temperature below 30° C. Ethyl acetate (4 vol) was then charged and the mixture was stirred and layers separated. Ethyl acetate (7 vol) was again charged to the aqueous layer and the contents were stirred and separated. Ethyl acetate (7 vol) was charged again to the aqueous layer and the contents were stirred and separated. The organic layers were combined and washed with water (4 vol) 4 times and stirred overnight at 20-25° C. The organic layers were then concentrated under heat and vacuum to 120 mL. The vessel contents were then heated to 50° C. and heptanes (120 mL) were added slowly. After addition of heptanes, the vessel contents were heated to reflux then cooled to 0° C. and held for ~2 hrs. The solids were filtered and rinsed with heptanes (2×2 vol). The solid product was then dried under vacuum at 30° C. to obtain N-{3-[5-(2-chloro-4-pyrimidinyl)-2-(1,1-dimethylethyl)-1,3-thiazol-4-yl]-2-fluorophenyl}-2,6-difluorobenzenesulfonamide (28.8 g, 80%).

Step D: N-{3-[5-(2-amino-4-pyrimidinyl)-2-(1,1-dimethylethyl)-1,3-thiazol-4-yl]-2-fluorophenyl}-2,6-difluorobenzenesulfonamide In 1 gal pressure reactor, a mixture of N-{3-[5-(2-chloro-4-pyrimidinyl)-2-(1,1-dimethylethyl)-1,3-thiazol-4-yl]-2-fluorophenyl}-2,6-difluorobenzenesulfonamide (120 g) prepared in accordance with Step C, above, and ammonium hydroxide (28-30%, 2.4 L, 20 vol) was heated in the sealed pressure reactor to 98-103° C. and stirred at this temperature for 2 hours. The reaction was cooled slowly to room temperature (20° C.) and stirred overnight. The solids were filtered and washed with minimum amount of the mother liquor and dried under vacuum. The solids were added to a mixture of EtOAc (15 vol)/water (2 vol) and heated to complete dissolution at 60-70° C. and the aqueous layer was removed and discarded. The EtOAC layer was charged with water (1 vol) and neutralized with aq. HCl to ~pH 5.4-5.5. and added water (1 vol). The aqueous layer was removed and discarded at 60-70° C. The organic layer was washed with water (1 vol) at 60-70° C. and the aqueous layer was removed and discarded. The organic layer was filtered at 60° C. and concentrated to 3 volumes. EtOAc (6 vol) was charged into the mixture and heated and stirred at 72° C. for 10 min, then cooled to 20° C. and stirred overnight. EtOAc was removed via vacuum distillation to concentrate the reaction mixture to ~3 volumes. The reaction mixture was maintained at ~65-70° C. for ~30 mins. Product crystals having the same crystal form as those prepared in Example 58b (and preparable by the procedure of Example 58b), above, in heptanes slurry were charged. Heptane (9 vol) was slowly added at 65-70° C. The slurry was stirred at 65-70° C. for 2-3 hours and then cooled slowly to 0-5° C. The product was filtered, washed with EtOAc/heptane (3/1 v/v, 4 vol) and dried at 45° C. under vacuum to obtain N-{3-[5-(2-amino-4-pyrimidinyl)-2-(1,1-dimethylethyl)-1,3-thiazol-4-yl]-2-fluorophenyl}-2,6-difluorobenzenesulfonamide (102.3 g, 88%).

Method 4: Compound B (mesylate salt)—N-{3-[5-(2-amino-4-pyrimidinyl)-2-(1,1-dimethylethyl)-1,3-thiazol-4-yl]-2-fluorophenyl}-2,6-difluorobenzenesulfonamide methanesulfonate

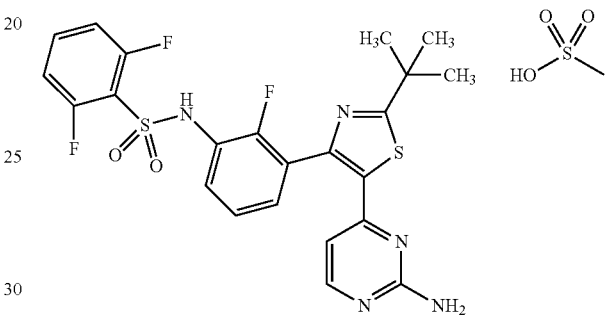

To a solution of N-{3-[5-(2-amino-4-pyrimidinyl)-2-(1,1-dimethylethyl)-1,3-thiazol-4-yl]-2-fluorophenyl}-2,6-difluorobenzenesulfonamide (204 mg, 0.393 mmol) in isopropanol (2 mL), methanesulfonic acid (0.131 mL, 0.393 mmol) was added and the solution was allowed to stir at room temperature for 3 hours. A white precipitate formed and the slurry was filtered and rinsed with diethyl ether to give the title product as a white crystalline solid (210 mg, 83% yield). $^1$H NMR (400 MHz, DMSO-d6) δ ppm 10.85 (s, 1H) 7.92-8.05 (m, 1H) 7.56-7.72 (m, 1H) 6.91-7.50 (m, 7H) 5.83-5.98 (m, 1H) 2.18-2.32 (m, 3H) 1.36 (s, 9H). MS (ESI): 520.0 [M+H]$^+$.

Method 5: Compound B (Alternative Mesylate Salt Embodiment)—N-{3-[5-(2-amino-4-pyrimidinyl)-2-(1,1-dimethylethyl)-1,3-thiazol-4-yl]-2-fluorophenyl}-2,6-difluorobenzenesulfonamide methanesulfonate N-{3-[5-(2-amino-4-pyrimidinyl)-2-(1,1-dimethylethyl)-1,3-thiazol-4-yl]-2-fluorophenyl}-2,6-difluorobenzenesulfonamide (as may be prepared according to example 58a) (2.37 g, 4.56 mmol) was combined with pre-filtered acetonitrile (5.25 vol, 12.4 mL). A pre-filtered solution of mesic acid (1.1 eq., 5.02 mmol, 0.48 g) in H$_2$O (0.75 eq., 1.78 mL) was added at 20° C. The temperature of the resulting mixture was raised to 50-60° C. while maintaining a low agitation speed. Once the mixture temperature reached to 50-60° C., a seed slurry of N-{3-[5-(2-amino-4-pyrimidinyl)-2-(1,1-dimethylethyl)-1,3-thiazol-4-yl]-2-fluorophenyl}-2,6-difluorobenzenesulfonamide methanesulfonate (1.0% w/w slurried in 0.2 vol of pre-filtered acetonitrile) was added, and the mixture was aged while agitating at a speed fast enough to keep solids from settling at 50-60° C. for 2 hr. The mixture was then cooled to 0-5° C. at 0.25° C./min and held at 0-5°

C. for at 6 hr. The mixture was filtered and the wet cake was washed twice with pre-filtered acetonitrile. The first wash consisted of 14.2 ml (6 vol) pre-filtered acetonitrile and the second wash consisted of 9.5 ml (4 vol) pre-filtered acetonitrile. The wet solid was dried at 50° C. under vacuum, yielding 2.39 g (85.1% yield) of product.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in a compound of the present invention. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention. Salts may be readily prepared by a person skilled in the art.

While it is possible that, for use in therapy, compounds A and B may be administered as the raw chemical, it is possible to present the active ingredient as a pharmaceutical composition. Accordingly, the invention further provides pharmaceutical compositions, which include a Compound A and/or a Compound B, and one or more pharmaceutically acceptable carriers, diluents, or excipients. The Compounds A and B are as described above. The carrier(s), diluent(s) or excipient(s) must be acceptable in the sense of being compatible with the other ingredients of the formulation, capable of pharmaceutical formulation, and not deleterious to the recipient thereof. In accordance with another aspect of the invention there is also provided a process for the preparation of a pharmaceutical composition including admixing a Compound A and/or Compound B, with one or more pharmaceutically acceptable carriers, diluents or excipients. Such elements of the pharmaceutical compositions utilized may be presented in separate pharmaceutical combinations or formulated together in one pharmaceutical composition. Accordingly, the invention further provides a combination of pharmaceutical compositions one of which includes Compound A and one or more pharmaceutically acceptable carriers, diluents, or excipients and a pharmaceutical composition containing Compound B and one or more pharmaceutically acceptable carriers, diluents, or excipients.

A pharmaceutical composition comprising Compound A and/or Compound B may be used in combination with a pharmaceutical composition comprising the PD-1 antagonist. Similarly, each of the agents in a combination of the invention may be formulated as separate pharmaceutical compositions for use in combination with each other.

Pharmaceutical compositions may be presented in unit dose forms containing a predetermined amount of active ingredient per unit dose. As is known to those skilled in the art, the amount of active ingredient per dose will depend on the condition being treated, the route of administration and the age, weight and condition of the patient. Preferred unit dosage compositions are those containing a daily dose or sub-dose, or an appropriate fraction thereof, of an active ingredient. Furthermore, such pharmaceutical compositions may be prepared by any of the methods well known in the pharmacy art.

Compounds A and B may be administered by any appropriate route. Suitable routes include oral, rectal, nasal, topical (including buccal and sublingual), vaginal, and parenteral (including subcutaneous, intramuscular, intraveneous, intradermal, intrathecal, and epidural). It will be appreciated that the preferred route may vary with, for example, the condition of the recipient of the combination and the cancer to be treated. It will also be appreciated that each of the agents administered may be administered by the same or different routes and that the Compounds A and B may be compounded together or in separate pharmaceutical compositions.

Any biotherapeutic agent in a combination of the invention, such as an anti-PD-1 antibody, may be administered parenterally, including by intravenous (IV) infusion and subcutaneous injection.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also to granulating, the powder mixture can be run through the tablet machine and the result is imperfectly formed slugs broken into granules. The granules can be lubricated be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, compositions for oral administration can be microencapsulated. The composition can also be prepared to prolong or sustain the release as for example by coating or embedding particulate material in polymers, wax or the like.

The agents for use according to the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Agents for use according to the present invention may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists that may be generated by means of various types of metered dose pressurised aerosols, nebulizers or insufflators.

Pharmaceutical compositions adapted for vaginal administration may be presented as pessaries, tampons, creams, gels, pastes, foams or spray compositions.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

When the PD-1 antagonist is a biotherapeutic agent, e.g., a monoclonal antibody that binds to PD-1 or PD-L1, the antagonist may be produced in CHO cells using conventional cell culture and then isolated using conventional recovery/purification technologies. A pharmaceutical composition comprising an anti-PD-1 antibody as the PD-1 antagonist may be provided as a liquid formulation or prepared by reconstituting a lyophilized powder with sterile water for injection prior to use. WO 2012/135408 describes the preparation of liquid and lyophilized medicaments comprising MK-3475 that are suitable for use in the present invention. In some preferred embodiments, a medicament comprising MK-3475 is provided in a glass vial which contains about 50 mg of MK-3475.

It should be understood that in addition to the ingredients particularly mentioned above, the compositions may include other agents conventional in the art having regard to the type of formulation in question, for example those suitable for oral administration may include flavoring agents.

Compounds A and B may be employed in combination in accordance with the invention by administration simultaneously in a unitary pharmaceutical composition including both compounds. Alternatively, the combination may be administered separately in separate pharmaceutical compositions, each including one of the compounds A and B in a sequential manner wherein, for example, Compound A or Compound B is administered first and the other second. Such sequential administration may be close in time (eg. simultaneously) or remote in time. Furthermore, it does not matter if the compounds are administered in the same dosage form, e.g. one compound may be administered topically and the other compound may be administered orally. Suitably, both compounds are administered orally.

Thus in one embodiment, one or more doses of Compound A are administered simultaneously or separately with one or more doses of Compound B and one or more doses of a PD-1 antagonist.

In one embodiment, multiple doses of Compound A are administered simultaneously or separately with multiple doses of Compound B and multiple doses of MK-3475 or an antigen binding fragment thereof.

In one embodiment, multiple doses of Compound A are administered simultaneously or separately with one dose of Compound B and one dose of nivolumab or an antigen binding fragment thereof or MK-3475 or an antigen binding fragment thereof.

In all the above embodiments, Compound A may be administered first or Compound B may be administered first or the PD-1 antagonist may be administered first.

The combinations may be presented as a combination kit. By the term "combination kit" "or kit of parts" as used herein is meant the pharmaceutical composition or compositions that are used to administer Compound B, and/or Compound A, and the PD-1 antagonist, e.g., an anti-PD-1 antibody or antigen binding fragment thereof, according to a dosage protocol of the invention. When compounds A, B, and an anti-PD-1 antibody or antigen binding fragment thereof are administered simultaneously, the combination kit can contain Compound A and Compound B in a single pharmaceutical composition or in separate pharmaceutical compositions, such as a tablet, and nivolumab or an antigen binding fragment thereof or MK-3475 or an antigen binding fragment thereof in a vial. When Compounds A and B are not administered simultaneously, the combination kit can contain Compound B, and/or Compound A in separate pharmaceutical compositions and another pharmaceutical composition comprising nivolumab or an antigen binding fragment thereof or MK-3475 or an antigen binding fragment thereof, wherein Compound B and/or Compound A are either in a single package or Compound B and/or Compound A are in separate pharmaceutical compositions in separate packages.

In one embodiment combination kits are provided wherein said compound of Formula I or a pharmaceutically acceptable salt thereof is provided in tablet form suitable for oral administration. In one embodiment combination kits are provided wherein said compound of Formula II or a pharmaceutically acceptable salt thereof is provided in tablet form suitable for oral administration. In one embodiment combination kits are provided wherein said anti-PD-1 antibody or antigen binding fragment thereof is formulated for IV administration. In one embodiment combination kits are provided wherein said anti-PD-1 antibody or antigen binding fragment thereof is formulated for subcutaneous administration.

In one aspect there is provided a kit of parts comprising components:

Compound A in association with a pharmaceutically acceptable adjuvant, diluents or carrier; Compound B in association with a pharmaceutically acceptable adjuvant, diluents or carrier; and an anti-PD-1 antibody or antigen binding fragment thereof in association with a pharmaceutically acceptable adjuvant, diluents or carrier.

In one embodiment of the invention the kit of parts comprise the following components:

Compound B in association with a pharmaceutically acceptable adjuvant, diluents or carrier; and/or Compound A in association with a pharmaceutically acceptable adjuvant, diluents or carrier;

and an anti-PD-1 antibody or antigen binding fragment thereof, wherein the components are provided in a form which is suitable for sequential, separate and/or simultaneous administration.

In one embodiment the kit of parts comprises:

a first container comprising Compound B in association with a pharmaceutically acceptable adjuvant, diluent or carrier; and/or a second container comprising Compound A in association with a pharmaceutically acceptable adjuvant, diluent or carrier, and a third container comprising nivolumab or an antigen binding fragment thereof or MK-3475 or an antigen binding fragment thereof.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

The term "loading dose" as used herein will be understood to mean a single dose or short duration regimen of Compound B or Compound A or an anti-PD-1 antibody having a dosage higher than the maintenance dose administered to the subject to, for example, rapidly increase the blood concentration level of the drug. Suitably, a short duration regimen for use herein will be from: 1 to 14 days; suitably from 1 to 7 days; suitably from 1 to 3 days; suitably for three days; suitably for two days; suitably for one day. In some embodiments, the "loading dose" can increase the blood concentration of the drug to a therapeutically effective level. In some embodiments, the "loading dose" can increase the blood concentration of the drug to a therapeutically effective level in conjunction with a maintenance dose of the drug. The "loading dose" of Compound A and/or Compound B can be administered once per day, or more than once per day (e.g., up to 4 times per day). Suitably the "loading dose" of Compound A and/or Compound B will be administered once a day. Suitably, the loading dose will be an amount from 2 to 100 times the maintenance dose; suitably from 2 to 10 times; suitably from 2 to 5 times; suitably 2 times; suitably 3 times; suitably 4 times; suitably 5 times. Suitably, the loading dose will be administered for 1 to 7 days; suitably from 1 to 5 days; suitably from 1 to 3 days; suitably for 1 day; suitably for 2 days; suitably for 3 days, followed by a maintenance dosing protocol.

The term "maintenance dose" as used herein will be understood to mean a dose that is serially administered (for example; at least twice), and which is intended to either slowly raise blood concentration levels of the compound to a therapeutically effective level, or to maintain such a therapeutically effective level. The maintenance dose for Compound A and/or Compound B is generally administered once per day and the daily dose of the maintenance dose is lower than the total daily dose of the loading dose.

Suitably the combinations of this invention are administered within a "specified period".

By the term "specified period" and derivatives thereof, as used herein is meant the interval of time between the administration of the first compound of the combination and last compound of the combination. For example, if Compound A is administered first, Compound B second and an anti-PD-1 antibody or antigen binding fragment thereof third, the time interval between administration of Compound A and the anti-PD-1 antibody or antigen binding fragment thereof is the specified period. When one component of the invention is administered more than once a day, the specified period is calculated based on the first administration of each component on a specific day. All administrations of a compound of the invention that are subsequent to the first during a specific day are not considered when calculating the specific period.

Suitably, if Compound A, optionally Compound B, and an anti-PD-1 antibody or antigen binding fragment thereof are administered within a "specified period" and not administered simultaneously, they are both administered within about 24 hours of each other—in this case, the specified period will be about 24 hours; suitably they will be administered within about 12 hours of each other—in this case, the specified period will be about 12 hours; suitably they will be administered within about 11 hours of each other—in this case, the specified period will be about 11 hours; suitably they will be administered within about 10 hours of each other—in this case, the specified period will be about 10 hours; suitably they will be administered within about 9 hours of each other—in this case, the specified period will be about 9 hours; suitably they will be administered within about 8 hours of each other—in this case, the specified period will be about 8 hours; suitably they will be administered within about 7 hours of each other—in this case, the specified period will be about 7 hours; suitably they will be administered within about 6 hours of each other—in this case, the specified period will be about 6 hours; suitably they will be administered within about 5 hours of each other—in this case, the specified period will be about 5 hours; suitably they will be administered within about 4 hours of each other—in this case, the specified period will be about 4 hours; suitably they will be administered within about 3 hours of each other—in this case, the specified period will be about 3 hours; suitably they will be administered within about 2 hours of each other—in this case, the specified period will be about 2 hours; suitably they will be administered within about 1 hour of each other—in this case, the specified period will be about 1 hour, and is considered simultaneous administration.

Suitably, when the combination of the invention is administered for a "specified period," the compounds will be co-administered for a "duration of time".

By the term "duration of time" and derivatives thereof, when used herein regarding Compound B and/or Compound A, is meant that Compound A and optionally Compound B are administered for an indicated number of consecutive days, optionally followed by a number of consecutive days where only one of the component compounds is administered.

By the term "duration of time" and derivatives thereof, when used herein regarding anti-PD-1 antibody or antigen binding fragment thereof, is meant that the anti-PD-1 antibody or antigen binding fragment thereof is administered once a week for an indicated number of consecutive weeks.

Regarding "Specified Period" Administration:

Suitably, Compound A, optionally Compound B and an anti-PD-1 antibody or antigen binding fragment thereof will be administered within a specified period for at least one day—in this case, the duration of time will be at least one day; suitably, during the course of treatment, Compound A, optionally Compound B and the anti-PD-1 antibody or antigen binding fragment thereof will be administered within a specified period for at least 3 consecutive days, where the anti-PD-1 antibody or antigen binding fragment thereof may optionally be administered once during this period—in this case, the duration of time will be at least 3 days; suitably, during the course of treatment, Compound A, optionally Compound B and an anti-PD-1 antibody or antigen binding fragment thereof will be administered within a specified period for at least 5 consecutive days, where the anti-PD-1 antibody or antigen binding fragment thereof may optionally be administered once during this period—in this case, the duration of time will be at least 5 days; suitably, during the course of treatment, Compound A, optionally Compound B and an anti-PD-1 antibody or antigen binding fragment thereof will be administered within a specified period for at least 7 consecutive days, where the anti-PD-1 antibody or antigen binding fragment thereof may optionally be administered once during this period—in this case, the duration of time will be at least 7 days; suitably, during the course of treatment, Compound A, optionally Compound B and an anti-PD-1 antibody or antigen binding fragment thereof will be administered within a specified period for at least 14 consecutive days, where the anti-PD-1 antibody or antigen binding fragment thereof may optionally be administered once a week during this period—in this case, the duration of time will be at least 14 days; suitably, during the course of treatment, Compound A, optionally Compound B and an anti-PD-1 antibody or antigen binding fragment thereof will be administered within a specified period for at least 28 consecutive days, where the anti-PD-1 antibody or antigen binding fragment thereof may optionally be administered once a week during this period—in this case, the duration of time will be at least 28 days.

Suitably, if the components are not administered during a "specified period," they are administered sequentially. By the term "sequential administration," and derivates thereof, as used herein is meant that the first component of the combination of Compound A, optionally Compound B or an anti-PD-1 antibody or antigen binding fragment thereof is administered for two or more consecutive days, followed by administration of a second component in the combination for two or more consecutive days, then followed by administration of the last component in the combination for two or more consecutive days. Also, contemplated herein is a drug holiday utilized among the sequential administration of Compound A, optionally Compound B and an anti-PD-1 antibody or antigen binding fragment thereof. As used herein, a drug holiday is a period of days after the sequential administration of one of Compound A, optionally Compound B and an anti-PD-1 antibody or antigen binding fragment thereof and before the administration of the other component of the invention. Suitably the drug holiday will be a period of days selected from: 1 day, 2 days, 3 days, 4 days, 5 days, 6 days, 7 days, 8 days, 9 days, 10 days, 11 days, 12 days, 13 days and 14 days.

Regarding Sequential Administration:

Suitably, Compound B will be administered first in the sequence, followed by an optional drug holiday, followed by administration of Compound A, followed by administration of an anti-PD-1 antibody or antigen binding fragment thereof. Suitably, Compound B is administered for 1 to 30 consecutive days, followed by an optional drug holiday, followed by administration of Compound A for 1 to 30 consecutive days, followed by an optional drug holiday, followed by administration of an anti-PD-1 antibody or antigen binding fragment thereof once a week for 1 to 10 weeks. Suitably, Compound B is administered for 1 to 21 consecutive days, followed by an optional drug holiday, followed by administration of Compound A for 1 to 21 consecutive days, followed by an optional drug holiday, followed by administration of an anti-PD-1 antibody or antigen binding fragment thereof once a week for 1 to 10 weeks. Suitably, Compound B is administered for 1 to 14 consecutive days, followed by an optional drug holiday, followed by administration of Compound A for 1 to 14 consecutive days, followed by an optional drug holiday, followed by administration of an anti-PD-1 antibody or antigen binding fragment thereof once a week for 1 to 10 weeks. Suitably, Compound B is administered for 14 consecutive days, followed by an optional drug holiday, followed by administration of Compound A for 7 consecutive days, followed by an optional drug holiday, followed by administration of an anti-PD-1 antibody or antigen binding fragment thereof once a week for 1 to 10 weeks. Suitably, Compound B is administered for 7 consecutive days, followed by an optional drug holiday, followed by administration of Compound A for 7 consecutive days, followed by an optional drug holiday, followed by administration of an anti-PD-1 antibody or antigen binding fragment thereof once a week for 1 to 10 weeks.

Suitably, Compound A will be administered first in the sequence, followed by an optional drug holiday, followed by optional administration of Compound B, followed by administration of an anti-PD-1 antibody or antigen binding fragment thereof. Suitably, Compound A is administered for 1 to 30 consecutive days, followed by an optional drug holiday, followed by optional administration of Compound B for 1 to 30 consecutive days, followed by an optional drug holiday, followed by administration of an anti-PD-1 antibody or antigen binding fragment thereof once a week for 1 to 10 weeks. Suitably, Compound A is administered for 1 to 21 consecutive days, followed by an optional drug holiday, followed by optional administration of Compound B for 1 to 21 consecutive days, followed by an optional drug holiday, followed by administration of an anti-PD-1 antibody or antigen binding fragment thereof once a week for 1 to 10 weeks. Suitably, Compound A is administered for 1 to 14 consecutive days, followed by an optional drug holiday, followed by optional administration of Compound B for 1 to 14 consecutive days, followed by an optional drug holiday, followed by administration of an anti-PD-1 antibody or antigen binding fragment thereof once a week for 1 to 10 weeks. Suitably, Compound A is administered for 14 consecutive days, followed by an optional drug holiday, followed by optional administration of Compound B for 14 consecutive days, followed by an optional drug holiday, followed by administration of an anti-PD-1 antibody or antigen binding fragment thereof once a week for 1 to 10 weeks. Suitably, Compound A is administered for 7 consecutive days, followed by an optional drug holiday, followed by optional administration of Compound B for 7 consecutive days, followed by an optional drug holiday, followed by administration of an anti-PD-1 antibody or antigen binding fragment thereof once a week for 1 to 10 weeks.

Suitably, an anti-PD-1 antibody or antigen binding fragment thereof will be administered first in the sequence, followed by an optional drug holiday, followed by optional administration of Compound B, followed by an optional drug holiday, followed by administration of Compound A.

Suitably, an anti-PD-1 antibody or antigen binding fragment thereof is administered once a week for from 1-10 weeks, followed by an optional drug holiday, followed by optional administration of Compound B for 1 to 30 consecutive days, followed by an optional drug holiday, followed by administration of Compound A for 1 to 30 consecutive days. Suitably, an anti-PD-1 antibody or antigen binding fragment thereof is administered once a week for from 1-10 weeks, followed by an optional drug holiday, followed by optional administration of Compound B for 1 to 21 consecutive days, followed by an optional drug holiday, followed by administration of Compound A for 1 to 21 consecutive days. Suitably, an anti-PD-1 antibody or antigen binding fragment thereof is administered once a week for from 1-10 weeks, followed by an optional drug holiday, followed by optional administration of Compound B for 1 to 14 consecutive days, followed by an optional drug holiday, followed by administration of Compound A for 1 to 14 consecutive days. Suitably, an anti-PD-1 antibody or antigen binding fragment thereof is administered once a week for from 1-10 weeks, followed by an optional drug holiday, followed by optional administration of Compound B for 14 consecutive days, followed by an optional drug holiday, followed by administration of Compound A for 14 consecutive days. Suitably, an anti-PD-1 antibody or antigen binding fragment thereof is administered once a week for from 1-10 weeks, followed by an optional drug holiday, followed by optional administration of Compound B for 7 consecutive days, followed by an optional drug holiday, followed by administration of Compound A for 7 consecutive days.

Suitably, an anti-PD-1 antibody or antigen binding fragment thereof will be administered first in the sequence, followed by an optional drug holiday, followed by administration of Compound A, followed by an optional drug holiday, followed by optional administration of Compound B. Suitably, an anti-PD-1 antibody or antigen binding fragment thereof is administered once a week for 1-10 weeks, followed by an optional drug holiday, followed by administration of Compound A for 1 to 30 consecutive days, followed by an optional drug holiday, followed by optional administration of Compound B for 1 to 30 consecutive days. Suitably, an anti-PD-1 antibody or antigen binding fragment thereof is administered once a week for from 1-10 weeks, followed by an optional drug holiday, followed by administration of Compound A for 1 to 21 consecutive days, followed by an optional drug holiday, followed by optional administration of Compound B for 1 to 21 consecutive days. Suitably, an anti-PD-1 antibody or antigen binding fragment thereof is administered once a week for 1-10 weeks, followed by an optional drug holiday, followed by administration of Compound A for 1 to 14 consecutive days, followed by an optional drug holiday, followed by optional administration of Compound B for 1 to 14 consecutive days. Suitably, an anti-PD-1 antibody or antigen binding fragment thereof is administered once a week for from 1-10 weeks, followed by an optional drug holiday, followed by administration of Compound A for 14 consecutive days, followed by an optional drug holiday, followed by optional administration of Compound B for 14 consecutive days. Suitably, an anti-PD-1 antibody or antigen binding fragment thereof is administered once a week for from 1-10 weeks, followed by an optional drug holiday, followed by administration of Compound A for 7 consecutive days, followed by an optional drug holiday, followed by optional administration of Compound B for 7 consecutive days.

Suitably, Compound A will be administered first in the sequence, followed by an optional drug holiday, followed by administration of an anti-PD-1 antibody or antigen binding fragment thereof, followed by optional administration of Compound B. Suitably, Compound A is administered for 1 to 30 consecutive days, followed by an optional drug holiday, followed by administration of an anti-PD-1 antibody or antigen binding fragment thereof once a week for 1 to 10 weeks, followed by an optional drug holiday, followed by optional administration of Compound B for 1 to 30 consecutive days. Suitably, Compound A is administered for 1 to 21 consecutive days, followed by an optional drug holiday, followed by administration of an anti-PD-1 antibody or antigen binding fragment thereof once a week for 1 to 10 weeks, followed by an optional drug holiday, followed by optional administration of Compound B for 1 to 21 consecutive days. Suitably, Compound A is administered for 1 to 14 consecutive days, followed by an optional drug holiday, followed by administration of an anti-PD-1 antibody or antigen binding fragment thereof once a week for 1 to 10 weeks, followed by an optional drug holiday, followed by optional administration of Compound B for 1 to 14 consecutive days. Suitably, Compound A is administered for 14 consecutive days, followed by an optional drug holiday, followed by administration of an anti-PD-1 antibody or antigen binding fragment thereof once a week for 1 to 10 weeks, followed by an optional drug holiday, followed by optional administration of Compound B for 14 consecutive days. Suitably, Compound A is administered for 7 consecutive days, followed by an optional drug holiday, followed by administration of an anti-PD-1 antibody or antigen binding fragment thereof once a week for 1 to 10 weeks, followed by an optional drug holiday, followed by optional administration of Compound B for 7 consecutive days.

Suitably, Compound B will be administered first in the sequence, followed by an optional drug holiday, followed by administration of an anti-PD-1 antibody or antigen binding fragment thereof, followed by administration of Compound A. Suitably, Compound B is administered for 1 to 30 consecutive days, followed by an optional drug holiday, followed by administration of an anti-PD-1 antibody or antigen binding fragment thereof once a week for 1 to 10 weeks, followed by an optional drug holiday, followed by administration of Compound A for 1 to 30 consecutive days. Suitably, Compound B is administered for 1 to 21 consecutive days, followed by an optional drug holiday, followed by administration of an anti-PD-1 antibody or antigen binding fragment thereof once a week for 1 to 10 weeks, followed by an optional drug holiday, followed by administration of Compound A for 1 to 21 consecutive days. Suitably, Compound B is administered for 1 to 14 consecutive days, followed by an optional drug holiday, followed by administration of an anti-PD-1 antibody or antigen binding fragment thereof once a week for 1 to 10 weeks, followed by an optional drug holiday, followed by administration of Compound A for 1 to 14 consecutive days. Suitably, Compound B is administered for 14 consecutive days, followed by an optional drug holiday, followed by administration of an anti-PD-1 antibody or antigen binding fragment thereof once a week for 1 to 10 weeks, followed by an optional drug holiday, followed by administration of Compound A for 14 consecutive days. Suitably, Compound B is administered for 7 consecutive days, followed by an optional drug holiday, followed by administration of an anti-PD-1 antibody or antigen binding fragment thereof once a week for 1 to 10 weeks, followed by an optional drug holiday, followed by administration of Compound A for 7 consecutive days.

It is understood that a "specified period" administration and a "sequential" administration can be followed by repeat dosing or can be followed by an alternate dosing protocol, and a drug holiday may precede the repeat dosing or alternate dosing protocol.

Suitably, the amount of Compound A (based on weight of unsalted/unsolvated amount) administered as part of the combination according to the present invention will be an amount selected from about 0.125 mg to about 10 mg; suitably, the amount will be selected from about 0.25 mg to about 9 mg; suitably, the amount will be selected from about 0.25 mg to about 8 mg; suitably, the amount will be selected from about 0.5 mg to about 8 mg; suitably, the amount will be selected from about 0.5 mg to about 7 mg; suitably, the amount will be selected from about 1 mg to about 7 mg; suitably, the amount will be about 5 mg. Accordingly, the amount of Compound A administered as part of the combination according to the present invention will be an amount selected from about 0.125 mg to about 10 mg. For example, the amount of Compound A administered as part of the combination according to the present invention can be 0.125 mg, 0.25 mg, 0.5 mg, 0.75 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg.

Suitably, the selected amount of Compound A is administered from 1 to 4 times a day. Suitably, the selected amount of Compound A is administered twice a day. Suitably, the selected amount of Compound A is administered once a day. Suitably, the administration of Compound A will begin as a loading dose. Suitably, the loading dose will be an amount from 2 to 100 times the maintenance dose; suitably from 2 to 10 times; suitably from 2 to 5 times; suitably 2 times; suitably 3 times; suitably 4 times; suitably 5 times. Suitably, the loading does will be administered from 1 to 7 days; suitably from 1 to 5 days; suitably from 1 to 3 days; suitably for 1 day; suitably for 2 days; suitably for 3 days, followed by a maintenance dosing protocol.

Suitably, the amount of Compound B (based on weight of unsalted/unsolvated amount) optionally administered as part of the combination according to the present invention will be an amount selected from about 10 mg to about 600 mg. Suitably, the amount will be selected from about 30 mg to about 300 mg; suitably, the amount will be selected from about 30 mg to about 280 mg; suitably, the amount will be selected from about 40 mg to about 260 mg; suitably, the amount will be selected from about 60 mg to about 240 mg; suitably, the amount will be selected from about 80 mg to about 220 mg; suitably, the amount will be selected from about 90 mg to about 210 mg; suitably, the amount will be selected from about 100 mg to about 200 mg, suitably, the amount will be selected from about 110 mg to about 190 mg, suitably, the amount will be selected from about 120 mg to about 180 mg, suitably, the amount will be selected from about 130 mg to about 170 mg, suitably, the amount will be selected from about 140 mg to about 160 mg, suitably, the amount will be 150 mg. Accordingly, the amount of Compound B administered as part of the combination according to the present invention will be an amount selected from about 10 mg to about 300 mg. For example, the amount of Compound B administered as part of the combination according to the present invention is suitably selected from 10 mg, 20 mg, 30 mg, 40 mg, 50 mg, 60 mg, 70 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg and 300 mg. Suitably, the selected amount of Compound B is administered from 1 to 4 times a day. Suitably, the selected amount of Compound B is administered twice a day. Suitably, Compound B is administered twice a day. Suitably, the selected amount of Compound B is administered once a day.

Suitably, the administration of Compound B will begin as a loading dose. Suitably, the loading dose will be an amount from 2 to 100 times the maintenance dose; suitably from 2 to 10 times; suitably from 2 to 5 times; suitably 2 times; suitably 3 times; suitably 4 times; suitably 5 times. Suitably, the loading does will be administered from 1 to 7 days; suitably from 1 to 5 days; suitably from 1 to 3 days; suitably for 1 day; suitably for 2 days; suitably for 3 days, followed by a maintenance dosing protocol.

An anti-PD-1 antibody or antigen binding fragment thereof is administered at a dosage amount of from about 50 mg/m$^2$/week to about 700 mg/m$^2$/week; suitably, from 100 mg/m$^2$/week to about 600 mg/m$^2$/week; suitably, from 200 mg/m$^2$/week to about 500 mg/m$^2$/week or at a dose of 1, 2, 3, 5 or 10 mg/kg at intervals of about 14 days (±2 days) or about 21 days (±2 days) or about 30 days (±2 days) throughout the course of treatment.

In an embodiment, an anti-PD-1 antibody or antigen binding fragment thereof is administered once a week with initial administration being in an amount of from 400 mg/m$^2$/week to about 500 mg/m$^2$/week and each subsequent administration being in an amount of from 200 mg/m$^2$/week to 300 mg/m$^2$/week. In one embodiment, an anti-PD-1 antibody is administered at a dose of about 0.3 to about 3.0 mg/kg up to about 10 mg/kg. Anti-PD-1 antibodies or antigen binding fragments thereof of the present invention can be formulation for intravenous administration and/or subcutaneous administration. Doses can be administered daily, weekly, once every two weeks, once every three weeks, once every four weeks, and/or monthly.

The present invention also provides a medicament which comprises a PD-1 antagonist as described above and a pharmaceutically acceptable excipient. When the PD-1 antagonist is a biotherapeutic agent, e.g., a mAb, the antagonist may be produced in CHO cells using conventional cell culture and recovery/purification technologies.

In some embodiments, a medicament comprising an anti-PD-1 antibody as the PD-1 antagonist may be provided as a liquid formulation or prepared by reconstituting a lyophilized powder with sterile water for injection prior to use. WO 2012/135408 describes the preparation of liquid and lyophilized medicaments comprising MK-3475 that are suitable for use in the present invention. In some preferred embodiments, a medicament comprising MK-3475 is provided in a glass vial which contains about 50 mg of MK-3475.

One embodiment of the present invention provides a combination of Compound A, administered once a day; Compound B, optionally administered once or twice a day; and MK-3475 administered according to the aforementioned protocol, for a period of at least 8 weeks, suitably for a period of at least 4 weeks, suitably for a period of at least 2 weeks, suitably for a period of at least 10 days, suitably for a period of at least 7 days, suitably all three compounds are administered on the first day of each 7 day period.

One embodiment of the present invention provides a combination of Compound A, administered once a day; Compound B, optionally administered once or twice a day; and nivolumab administered according to the aforementioned protocol, for a period of at least 8 weeks, suitably for a period of at least 4 weeks, suitably for a period of at least 2 weeks, suitably for a period of at least 10 days, suitably for a period of at least 7 days, suitably all three compounds are administered on the first day of each 7 day period.

As used herein, all amounts specified for Compound A and Compound B are indicated as the amount of free or unsalted compound.

In some embodiments of any of the above pharmaceutical compositions, combinations, combination kits, uses and treatment methods, Compound A is administered once daily as a 2-mg MEKINIST (trametinib) tablet, Compound B is administered twice daily as two 75-mg or three 50-mg TANIFLAR (dabrafenib) capsules, and the PD-1 antagonist is MK-3475, which is administered by intravenous infusion once every three weeks at a dose of 2 mg/kg or once every 2 weeks at a dose of 10 mg/kg.

Method of Treatment

The combinations and combination therapies of the invention are believed to have utility in disorders wherein the inhibition of BRAF and/or MEK and/or enhancement of the immune response through blocking the inhibitory signal of PD-1 is beneficial.

The present invention thus also provides a combination of the invention, for use in therapy, particularly in the treatment of disorders wherein the inhibition of BRAF and/or MEK and/or enhancing the immune response by blocking the inhibitory signaling of PD-1 is beneficial, particularly cancer.

A further aspect of the invention provides a method of treatment of a disorder wherein inhibition of BRAF and/or MEK and/or enhancing the immune response by blocking the inhibitory signaling of PD-1 is beneficial, comprising administering a combination of the invention.

A further aspect of the present invention provides the use of a combination of the invention in the manufacture of a medicament for the treatment of a disorder wherein the inhibition of BRAF and/or MEK and/or enhancing the immune response by blocking the inhibitory signaling of PD-1 is beneficial.

Typically, the disorder is a cancer such that inhibition of BRAF and/or MEK and/or enhancing the immune response by blocking the inhibitory signaling of PD-1 has a beneficial effect. Examples of cancers that are suitable for treatment with combination of the invention include, but are limited to, both primary and metastatic forms of head and neck, breast, lung, colon, ovary, and prostate cancers. Suitably the cancer is selected from: brain (gliomas), glioblastomas, astrocytomas, glioblastoma multiforme, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, lymphoblastic T cell leukemia, Chronic myelogenous leukemia, Chronic lymphocytic leukemia, Hairy-cell leukemia, acute lymphoblastic leukemia, acute myelogenous leukemia, AML, Chronic neutrophilic leukemia, Acute lymphoblastic T cell leukemia, plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Additionally, examples of a cancer to be treated include Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers.

Suitably, the present invention relates to a method for treating or lessening the severity of a cancer selected from: brain (gliomas), glioblastomas, astrocytomas, glioblastoma multiforme, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

Suitably, the present invention relates to a method for treating or lessening the severity of a cancer selected from ovarian, breast, pancreatic and prostate.

Suitably the present invention relates to a method for treating or lessening the severity of pre-cancerous syndromes in a mammal, including a human, wherein the pre-cancerous syndrome is selected from: cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

Suitably, the present invention relates to a method of treating or lessening the severity of a cancer that is either wild type or mutant for Raf and KRAS and either wild type or mutant for PI3K/Pten. This includes patients with a cancer that is wild type for both Raf, KRAS, and PI3K/PTEN, mutant for Raf, KRAS and PI3K/PTEN, mutant for Raf and wild type for KRAS and PI3K/PTEN and wild type for Raf and KRAS and mutant for PI3K/PTEN.

The term "wild type" as is understood in the art refers to a polypeptide or polynucleotide sequence that occurs in a native population without genetic modification. As is also understood in the art, a "mutant" includes a polypeptide or polynucleotide sequence having at least one modification to an amino acid or nucleic acid compared to the corresponding amino acid or nucleic acid found in a wild type polypeptide or polynucleotide, respectively. Included in the term mutant is Single Nucleotide Polymorphism (SNP) where a single base pair distinction exists in the sequence of a nucleic acid strand compared to the most prevalently found (wild type) nucleic acid strand. Suitably, when the cancer is wild type for Raf or BRAF wild type or tests negative for a BRAF V600 mutation, only Compound A and an anti-PD-1 antibody or antigen binding fragment thereof are administered, and Compound B is not administered.

Cancers that are either wild type or mutant for Raf, either wild type or mutant for PI3K/Pten, and either wild type or mutant are identified by known methods.

For example, wild type or mutant Raf or PI3K/PTEN tumor cells can be identified by DNA amplification and sequencing techniques, DNA and RNA detection techniques, including, but not limited to Northern and Southern blot, respectively, and/or various biochip and array technologies. Wild type and mutant polypeptides can be detected by a variety of techniques including, but not limited to immunodiagnostic techniques such as ELISA, Western blot or immunocytochemistry. Suitably, Pyrophosphorolysis-activated polymerization (PAP) and/or PCR methods may be used. Liu, Q et al; Human Mutation 23:426-436 (2004).

In one preferred embodiment, a patient with advanced or metastatic melanoma that tests positive for a BRAF V600 mutation is administered a combination of: (i) MK-3475 at a dose of 1 mg/kg Q3W, 2 mg/kg Q3W or 10 mg/kg Q2W; (ii) dabrafenib at a dose of 100 BID or 150 BID and (iii) trametinib at a dose of 1 mg or 2 mg QD.

In another preferred embodiment, a patient with advanced or metastatic melanoma that tests negative for a BRAF V600 mutation is administered a combination of: (i) MK-3475 at a dose of 2 mg/kg Q3W or 10 mg/kg Q2W and trametinib at a dose of 1 mg QD or 2 mg QD.

In yet another preferred embodiment, a patient with advanced or metastatic melanoma that tests positive for a BRAF V600 mutation is administered a combination of: (i) MK-3475 at a dose of 1 mg/kg Q3W, 2 mg/kg Q3W or 10 mg/kg Q2W and dabrafenib at a dose of 100 mg BID or 150 BID.

In any of the above preferred embodiments, the preferred starting doses are: MK-3475 at 2 mg/kg Q3W, dabrafenib at 150 mg BID and trametinib at 2 mg QD. If the patient experiences a kinase-inhibitor related adverse event during treatment with the combination, the dose of dabrafenib and/or trametinib is preferably reduced by up to one half the starting dose. If the patient experiences an immune related adverse event during treatment with the combination, the MK-3475 dose is reduced to one-half of the starting dose, e.g., 1 mg/kg Q3W.

In each of the above preferred embodiments for the treatment of advanced or metastatic melanoma, MK-3475 is preferably administered as a liquid pharmaceutical composition which comprises 25 mg/ml MK-3475, 7% (w/v) sucrose, 0.02% (w/v) polysorbate 80 in 10 mM histidine buffer pH 5.5, and the selected dose of the composition is administered by IV infusion over a time period of about 30 minutes (e.g., 25 to 40 minutes).

In any of the above embodiments for the treatment of advanced or metastatic melanoma, the combination is administered for at least one cycle of six weeks, and preferably the treatment duration is any of: at least 6, 12, 18 or 24 months, at least 2 cycles after a CR, and observation of PD.

In any of the above embodiments for the treatment of advanced or metastatic melanoma, the combination is administered to patients with a tumor that tests positive for PD-L1 expression.

In any of the above embodiments for treatment of advanced or metastatic melanoma, the patient preferably does not have a diagnosis of uveal or ocular melanoma, and preferably has not received prior systemic therapy for metastatic or advance melanoma with an agent targeting PD-1, PD-L1, CTLA4, BRAF, MEK or other molecules in the MAPK pathway.

The combination of the invention may be used alone or in combination with one or more other therapeutic agents. The invention thus provides in a further aspect a further combination comprising a combination of the invention with a further therapeutic agent or agents, compositions and medicaments comprising the combination and use of the further combination, compositions and medicaments in therapy, in particular in the treatment of diseases susceptible to inhibition of MEK and/or inhibition of BRAF and/or an enhanced immune response by blocking the inhibitory signaling of PD-1.

In one embodiment, a combination of the invention may be employed with other therapeutic methods of cancer treatment. In particular, in anti-neoplastic therapy, combination therapy with other chemotherapeutic, hormonal, antibody agents as well as surgical and/or radiation treatments other than those mentioned above are envisaged. Combination therapies according to the present invention thus include the administration of Compound A, Compound B and MK-3475 or nivolumab as well as optional use of other therapeutic agents including other anti-neoplastic agents. Such combination of agents may be administered together or separately and, when administered separately this may occur simultaneously or sequentially in any order, both close and remote in time. In one embodiment, the pharmaceutical combination includes Compound A, Compound B and MK-3475, and optionally at least one additional anti-neoplastic agent. In one embodiment, the pharmaceutical combination includes Compound A, Compound B and nivolumab, and optionally at least one additional anti-neoplastic agent.

In one embodiment, the further anti-cancer therapy is surgical and/or radiotherapy.

In one embodiment, the further anti-cancer therapy is at least one additional anti-neoplastic agent.

Any anti-neoplastic agent that has activity versus a susceptible tumor being treated may be utilized in the combination. Typical anti-neoplastic agents useful include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine angiogenesis inhibitors; immunotherapeutic agents; proapoptotic agents; and cell cycle signaling inhibitors.

Anti-microtubule or anti-mitotic agents: Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleuko-blastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes: Platinum coordination complexes are non-phase specific anti-cancer agents, which are interactive with DNA. The platinum complexes enter tumor cells, undergo, aquation and form intra- and inter-strand crosslinks with DNA causing adverse biological effects to the tumor. Examples of platinum coordination complexes include, but are not limited to, oxaliplatin, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer.

Carboplatin, platinum, diammine[1,1-cyclobutane-dicarboxylate(2+O,O'], is commercially available as PARAPLATIN® as an injectable solution. Carboplatin is primarily indicated in the first and second line treatment of advanced ovarian carcinoma.

Alkylating agents: Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease.

Busulfan, 1,4-butanediol dimethanesulfonate, is commercially available as MYLERAN® TABLETS. Busulfan is indicated for the palliative treatment of chronic myelogenous leukemia.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease.

Antibiotic anti-neoplastics: Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas.

Topoisomerase II inhibitors: Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite neoplastic agents: Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H)pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine).

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine, fludarabine phosphate, and cladribine.

Gemcitabine, 2'-deoxy-2',2'-difluorocytidine monohydrochloride ((β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Topoisomerase I inhibitors: Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazinomethylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-13]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer.

Hormones and hormonal analogues: Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors: Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by overexpression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets," New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-lacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-angiogenic agents: Anti-angiogenic agents including non-receptor angiogenesis inhibitors may also be useful. Anti-angiogenic agents such as those which inhibit the effects of vascular edothelial growth factor, (for example the anti-vascular endothelial cell growth factor antibody bevacizumab [Avastin™], and compounds that work by other mechanisms (for example linomide, inhibitors of integrin αvβ3 function, endostatin and angiostatin);

Immunotherapeutic agents: Agents used in immunotherapeutic regimens may also be useful in combination with the compounds of formula (I). Immunotherapy approaches, including for example ex-vivo and in-vivo approaches to increase the immunogenecity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies Proapoptotoc agents: Agents used in proapoptotic regimens (e.g., bcl-2 antisense oligonucleotides) may also be used in the combination of the present invention.

Cell cycle signalling inhibitors: Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the combination of the present invention comprises a compound of formula I or a salt or solvate thereof and at least one anti-neoplastic agent selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine angiogenesis inhibitors, immunotherapeutic agents, proapoptotic agents, and cell cycle signaling inhibitors.

In one embodiment, the combination of the present invention comprises a compound of formula I or a salt or solvate thereof and at least one anti-neoplastic agent which is an anti-microtubule agent selected from diterpenoids and vinca alkaloids.

In a further embodiment, the at least one anti-neoplastic agent is a diterpenoid.

In a further embodiment, the at least one anti-neoplastic agent is a vinca alkaloid.

In one embodiment, the combination of the present invention comprises a compound of formula I or a salt or solvate thereof and at least one anti-neoplastic agent, which is a platinum coordination complex.

In a further embodiment, the at least one anti-neoplastic agent is paclitaxel, carboplatin, or vinorelbine.

In a further embodiment, the at least one anti-neoplastic agent is carboplatin.

In a further embodiment, the at least one anti-neoplastic agent is vinorelbine.

In a further embodiment, the at least one anti-neoplastic agent is paclitaxel.

In one embodiment, the combination of the present invention comprises a compound of formula I and salts or solvates thereof and at least one anti-neoplastic agent which is a signal transduction pathway inhibitor.

In a further embodiment the signal transduction pathway inhibitor is an inhibitor of a growth factor receptor kinase VEGFR2, TIE2, PDGFR, BTK, erbB2, EGFr, IGFR-1, TrkA, TrkB, TrkC, or c-fms.

In a further embodiment the signal transduction pathway inhibitor is an inhibitor of a serine/threonine kinase rafk, akt, or PKC-zeta.

In a further embodiment the signal transduction pathway inhibitor is an inhibitor of a non-receptor tyrosine kinase selected from the src family of kinases.

In a further embodiment the signal transduction pathway inhibitor is an inhibitor of c-src.

In a further embodiment the signal transduction pathway inhibitor is an inhibitor of Ras oncogene selected from inhibitors of farnesyl transferase and geranylgeranyl transferase.

In a further embodiment the signal transduction pathway inhibitor is an inhibitor of a serine/threonine kinase selected from the group consisting of PI3K.

In a further embodiment the signal transduction pathway inhibitor is a dual EGFr/erbB2 inhibitor, for example N-{3-Chloro-4-[(3-fluorobenzyl)oxy]phenyl}-6-[5-({[2-(methanesulphonyl)ethyl]amino}methyl)-2-furyl]-4-quinazolinamine (structure below):

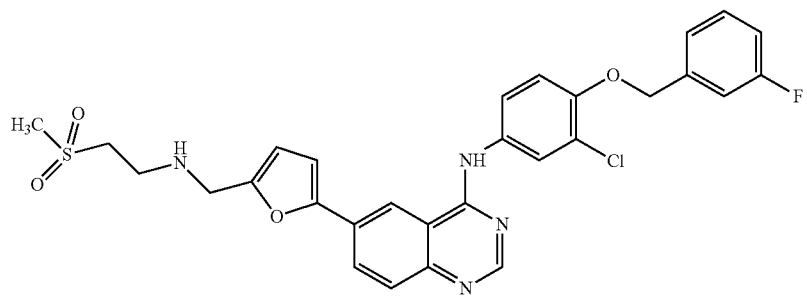 [SMILES: CS(=O)(=O)CCNCc1ccc(-c2ccc3ncnc(Nc4ccc(OCc5cccc(F)c5)c(Cl)c4)c3c2)o1]

In one embodiment, the combination of the present invention comprises a compound of formula I or a salt or solvate thereof and at least one anti-neoplastic agent which is a cell cycle signaling inhibitor.

In further embodiment, cell cycle signaling inhibitor is an inhibitor of CDK2, CDK4 or CDK6.

In one embodiment the mammal in the methods and uses of the present invention is a human.

As indicated, therapeutically effective amounts of the active components in combinations and combination therapies of the invention (a PD-1 antagonist and one or both of Compound A and Compound B) are administered to a human. Typically, the therapeutically effective amount of the administered agents of the present invention will depend upon a number of factors including, for example, the age and weight of the subject, the precise condition requiring treatment, the severity of the condition, the nature of the formulation, and the route of administration. Ultimately, the therapeutically effective amount will be at the discretion of the attendant physician.

The combinations of the present invention are tested for efficacy, advantageous and synergistic properties according to known procedures. Suitably, the combinations of the invention are tested for efficacy, advantageous and synergistic properties generally according to the following combination cell proliferation assays. Cells are plated in 384-well plates at 500 cells/well in culture media appropriate for each cell type, supplemented with 10% FBS and 1% penicillin/streptomycin, and incubated overnight at 37° C., 5% $CO_2$. Cells are treated in a grid manner with dilution of Compound A (20 dilutions, including no compound, of 2-fold dilutions starting from 1-20 mM depending of compound) from left to right on 384-well plate; and also optionally treated with Compound B (20 dilutions, including no compound, of 2-fold dilutions starting from 1-20 mM depending of compound) from top to bottom on 384-well plate; and also treated with an anti-PD-1 antibody or antigen binding fragment thereof and incubated as above for a further 72 hours. In some instances compounds are added in a staggered manner and incubation time can be extended up to 7 days. Cell growth is measured using CellTiter-Glo® reagent according to the manufacturer's protocol and signals are read on a PerkinElmer EnVision™ reader set for luminescence mode with a 0.5-second read. Data are analyzed as described below.

Results are expressed as a percentage of the t=0 value and plotted against compound(s) concentration. The t=0 value is normalized to 100% and represents the number of cells present at the time of compound addition. The cellular response is determined for each compound and/or compound combination using a 4- or 6-parameter curve fit of cell viability against concentration using the IDBS XLfit plug-in for Microsoft Excel software and determining the concentration required for 50% inhibition of cell growth ($gIC_{50}$). Background correction is made by subtraction of values from wells containing no cells. For each drug combination a Combination Index (CI), Excess Over Highest Single Agent (EOHSA) and Excess Over Bliss (EOBliss) are calculated according to known methods such as described in Chou and Talalay (1984) Advances in Enzyme Regulation, 22, 37 to 55; and Berenbaum, M C (1981) Adv. Cancer Research, 35, 269-335.

The combinations of the present invention are tested in the above assays to determine advantageous therapeutic utility in treating cancer.

The following examples are intended for illustration only and are not intended to limit the scope of the invention in any way.

Example 1—Kit Composition

The sucrose, microcrystalline cellulose and the compounds A and B of the invented combination, as shown in Tables I and II below, are individually mixed and granulated in the proportions shown with a 10% gelatin solution. The wet granules are screened, dried, mixed with the starch, talc and stearic acid, then screened and compressed into a tablet. A vial of MK-3475 is also included in the kit as described in Table III.

TABLE I

| INGREDIENTS | AMOUNTS |
|---|---|
| N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide dimethyl sulfoxide (the dimethyl sulfoxide solvate of Compound A) | 2 mg |
| Microcrystalline cellulose | 300 mg |
| Sucrose | 4 mg |
| Starch | 2 mg |
| Talc | 1 mg |
| stearic acid | 0.5 mg |

TABLE II

| INGREDIENTS | |
|---|---|
| N-{3-[5-(2-Amino-4-pyrimidinyl)-2-(1,1-dimethylethyl)-1,3-thiazol-4-yl]-2-fluorophenyl}-2,6-difluorobenzenesulfonamide methanesulfonate, (the methanesulfonate salt of Compound B) | 200 mg |
| Microcrystalline cellulose | 200 mg |
| Sucrose | 10 mg |
| Starch | 40 mg |
| Talc | 20 mg |
| stearic acid | 5 mg |

TABLE III

| |
|---|
| MK-3475 may be supplied as a solution consisting of 25 mg/ml MK-3475, 7% (w/v) Sucrose, 0.02% (w/v) polysorbate 80 in 10 mM histidine buffer pH 5.5. |

Example 2—Anti-Tumor Response of Concurrent Administration of a PD-1 Antagonist and Trametinib to Tumor-Bearing Mice This experiment compared the anti-tumor response of tumor-bearing mice to treatment with one of three regimens: (i) monotherapy with a murine anti-mouse PD-1 monoclonal antibody of murine isotype IgG1 (Anti-PD1); (ii) monotherapy with trametinib and (iii) combination therapy with anti-PD1 and trametinib administered concurrently. Murine isotype IgG1 is the murine counterpart isotype to human isotype IgG4.

While human tumor cells or tumor explants can be grown in immunodeficient animals as xenografts, they cannot be used for testing immunotherapeutics because of the lack of a functional immune system. For a meaningful evaluation of immunotherapeutics or combination of immunotherapeutics with other agents, it is necessary to use a syngeneic model in which syngeneic tumors are grown in animals with an intact immune system. CT-26 is a murine colorectal adenocarcinoma cell line syngeneic to the BALB/c mouse strain. CT-26 carries a KRAS mutation that activates the mitogen-activating protein kinase pathway, which makes it a relevant model to evaluate sensitivity to trametinib (an inhibitor of mitogen-activated protein kinase kinase). This is also a relevant model system for evaluating the mechanism of action for an anti-PD-1 antibody because of the translatable molecular profile of this tumor post-anti-PD-1 therapy.

Tumor-bearing mice for this study were initiated by implanting $3 \times 10^5$ log-phase and sub-confluent CT-26 cells on the right lower dorsal flank of 7-8 week old female BALB/c mice with an average body weight of 20 grams. When the mean tumor volume in these mice reached ~126 cubic mm (FIG. 8B, left panel marked Day 0), the tumor-bearing mice were randomized to 4 treatment groups of 12 mice per group: (1) Isotype+Vehicle control group; (2) Anti-PD1+Vehicle control; (3) trametinib+Isotype control and (4) Anti-PD1+trametinib. The Vehicle control was 0.5% HPMC (Hydroxypropylmethylcellulose, Sigma) and 0.2% Tween 80 (Sigma) in injection-grade water pH 8.0. The Isotype control was a mouse monoclonal antibody specific for adenoviral hexon 25 and was of the murine isotype IgG1. Anti-PD1 was administered to treatment groups 2 and 4 at 10 mg/kg i.p., every 5 days for each of 5 cycles, with the first dosing designated as Day 0 in FIG. 8. Trametinib was administered to treatment groups 3 and 4 at 1 mg/kg every day for 23 days, with the first dosing designated as Day 0 in FIG. 8.

Surprisingly, administration of trametinib, a potential T cell immunosuppressive agent, did not appear to antagonize the anti-tumor effects of Anti-PD1 in the combination treatment arm. In contrast, as demonstrated by the results shown in FIG. 8, the mean anti-tumor response of concurrent administration of Anti-PD1 and trametinib was greater (p<0.001) than the anti-tumor response observed with either single agent treatment. In addition, the combination therapy resulted in a complete regression (CR) (no measurable tumor) in 17% of the cohort (2 out of 12 animals) at the end of the 23 day treatment period, while no CRs were observed in the single agent treatment groups. Comparing mean tumor volumes at the end of the study (FIG. 8B, right panel) using one way ANOVA/Bonferroni, the tumor volumes of mice treated with the combination of trametinib+Anti-PD1 were significantly smaller than those treated with trametinib alone.

Example 3—Clinical Safety and Efficacy of a Combination of a PD-1 Antagonist, a MEK Inhibitor and a BRAF Inhibitor A Phase I/II Study is performed to Assess the Safety and Efficacy of MK-3475 in Combination with Trametinib and Dabrafenib in Subjects with Advanced Melanoma. This study is a multi-center, worldwide, Phase I/II 3-part trial of intravenous (IV) MK-3475 in combination with oral dabrafenib and/or trametinib in subjects with advanced or metastatic melanoma to be conducted in conformance with Good Clinical Practices.

Part 1 is a nonrandomized, multi-site, open-label portion of the study using a traditional 3+3 design for dose escalation to evaluate safety, tolerability, and dosing of MK-3475 in combination with dabrafenib and trametinib (MK+D+T) in BRAF mutation-positive (V600 E/K) melanoma subjects. Part 2 is a nonrandomized, multi-site, open-label portion of the study using expansion cohort(s) to further evaluate safety and confirm dose of (MK+D+T). Also in Part 2, expansion cohort(s) will be used to further evaluate safety and preliminary efficacy in the (MK+T) combination. Part 3 is a randomized (1:1), active-controlled, multi-site, two-arm study of the confirmed dose of the triplet combination (MK+D+T) versus placebo in combination with D+T (PBO+D+T). Subjects will be stratified by Eastern Cooperative Oncology Group (ECOG) Performance Scale (0 vs. 1) and Lactate Dehydrogenase (LDH) level (>1.1×ULN vs. ≤1.1×ULN). A more detailed summary of the study is presented in the table below.

| | |
|---|---|
| Clinical Indication | The treatment of subjects with advanced or metastatic melanoma |
| Trial Type | Interventional |
| Type of control | No treatment control in Parts 1 and 2. Placebo (standard, active therapy with a placebo add-on) in Part 3. |
| Route of administration | Intravenous (MK-3475) <br> Oral (trametinib) <br> Oral (dabrafenib) |
| Trial Blinding | Parts 1 and 2: Unblinded Open Label <br> Part 3: Double-blind |
| Treatment Groups | In Part 1 (3 + 3 design), cohorts of 3 or 6 subjects with BRAF mutant [V600 E/K] melanoma will receive escalating doses of MK-3475 in combination with trametinib 2 mg QD and dabrafenib 150 mg BID: <br> MK-3475 2 mg/kg q3 weeks <br> MK-3475 10 mg/kg q2 weeks <br> Additionally in Part 1 (3 + 3 design), cohorts of 3 or 6 subjects with BRAF wild type [without V600] melanoma will receive escalating doses of MK-3475 in combination with trametinib 2 mg QD: <br> MK-3475 2 mg/kg q3 weeks <br> MK-3475 10 mg/kg q2 weeks <br> Approximately 18 subjects will be enrolled in Part 1 (~9 for the (MK + D + T) combination therapy and ~9 for the (MK + T) combination therapy). <br> In Part 1, and only in the event dose level 1 is not tolerable in the (MK + D + T) combination therapy, cohorts of 3 or 6 subjects with BRAF mutant [V600 E/K] melanoma will receive escalating doses of MK-3475 in combination with dabrafenib 150 mg BID (3 + 3 design): <br> MK-3475 2 mg/kg q3 weeks <br> MK-3475 10 mg/kg q2 weeks <br> Approximately 9 subjects will be enrolled for the (MK + D) combination therapy, but only if dose level 1 is not tolerable in the (MK + D + T) combination. <br> Part 2 will expand cohort(s) from Part 1 for dose confirmation. Approximately 66 subjects will be enrolled in Part 2, ~20 for (MK + D + T) and ~46 for (MK + T). <br> In Part 3, approximately 120 subjects with BRAF mutant [V600 E/K] melanoma will be randomized 1:1 to either: (a) the confirmed dose of MK-3475, trametinib 2 mg QD, dabrafenib 150 mg BID, or, (b) placebo (saline IV), trametinib 2 mg QD, dabrafenib 150 mg BID. Note: The triplet dose combination of all treatments used in Part 3 will be confirmed by Parts 1 and 2 of the study. |
| Number of trial subjects | Approximately 89 subjects will be enrolled in the investigation of the (MK + D + T) combination therapy (this total includes subjects from specific arms in Parts 1 and 2, and subjects in the blinded active (MK + D + T) arm from Part 3). Additionally, 60 subjects will receive PBO (saline IV) + (D + T) in Part 3 of the study. ~55 subjects will be enrolled in the investigation of the (MK + T) combination therapy (Parts 1 and 2 only). In the overall study, ~204 subjects will be enrolled. |
| Estimated duration of trial | The sponsor estimates that the trial will require approximately 44 months from the time the first subject signs the informed consent until the last subject's last visit. |
| Duration of Participation | Each subject will participate in the trial from the time the subject signs the Informed Consent Form (ICF) through the final protocol-specified contact. After a screening phase of up to 28 days, eligible subjects will receive assigned treatment on Day 1 of the dosing cycle. Treatment with MK-3475, trametinib, and/or dabrafenib will continue until documented disease progression, unacceptable adverse event(s), intercurrent illness that prevents further administration of treatment, |

-continued

|  |  |
|---|---|
|  | investigator's decision to withdraw the subject, subject withdraws consent, pregnancy of the subject, noncompliance with trial treatment or procedure requirements, or administrative reasons. MK-3475 treated subjects who attain a complete response after at least 6 months of study treatment may consider stopping MK-3475 treatment (at the discretion of the investigator after receiving at least two doses beyond the initial determination of complete response), while continuing on treatment with trametinib and/or dabrafenib. Subjects who stop MK-3475 may be eligible for re-treatment after experiencing disease progression at the discretion of the investigator if they meet the criteria for re-treatment; this will be designated the Second Course Phase. MK-3475 treatment may continue for a maximum of 24 months. After the end of all treatments, each subject will be followed for a minimum of 30 days for adverse event monitoring (serious adverse events will be collected for up to 90 days after the end of treatment). Subjects will have post-treatment follow-up for disease status, including initiating a non-study cancer treatment and experiencing disease progression, until death, withdrawing consent, or becoming lost to follow-up. |
| Randomization Ratio | Part 3: 1:1 |

The table below provides a brief description of the sequences in the sequence listing.

| SEQ ID NO: | Description |
|---|---|
| 1 | hPD-1.08A light chain CDR1 |
| 2 | hPD-1.08A light chain CDR2 |
| 3 | hPD-1-08A light chain CDR3 |
| 4 | hPD-1.08A heavy chain CDR1 |
| 5 | hPD-1.08A heavy chain CDR2 |
| 6 | hPD-1.08A heavy chain CDR3 |
| 7 | hPD-1.09A light chain CDR1 |
| 8 | hPD-1.09A light chain CDR2 |
| 9 | hPD-1.09A light chain CDR3 |
| 10 | hPD-1.09A heavy chain CDR1 |
| 11 | hPD-1.09A heavy chain CDR2 |
| 12 | hPD-1.09A heavy chain CDR3 |
| 13 | 109A-H heavy chain variable region |
| 14 | 409A-H heavy chain full length |
| 15 | K09A-L-11 light chain variable region |
| 16 | K09A-L-16 light chain variable region |
| 17 | K09A-L-17 light chain variable region |
| 18 | K09A-L-11 light chain full length |
| 19 | K09A-L-16 light chain full length |
| 20 | K09A-L-17 light chain full length |
| 21 | MK-3475 Heavy chain |
| 22 | MK-3475 Light chain |
| 23 | Nivolumab Heavy chain |
| 24 | Nivolumab light chain |

While the preferred embodiments of the invention are illustrated by the above, it is to be understood that the invention is not limited to the precise instructions herein disclosed and that the right to all modifications coming within the scope of the following claims is reserved.

The invention claimed is:

1. A method of treating melanoma in a mammal comprising administering to said mammal a combination therapy, wherein the combination therapy comprises a therapeutically effective amount of an anti-human PD-1 antibody, a therapeutically effective amount of a Compound A and a therapeutically effective amount of a Compound B, wherein:

the anti-human PD-1 antibody comprises a heavy chain comprising the sequence of amino acids set forth in SEQ ID NO: 21 and a light chain comprising the sequence of amino acids set forth in SEQ ID NO: 22; the Compound B is a compound of structure (II):

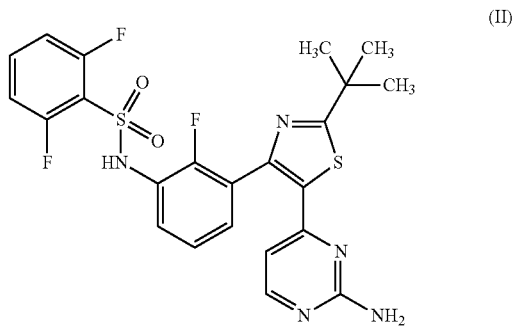 [SMILES: CC(C)(C)c1nc(-c2cccc(NS(=O)(=O)c3c(F)cccc3F)c2F)c(-c2ccnc(N)n2)s1]

or a pharmaceutically acceptable salt thereof; the Compound A is a compound of structure (I):

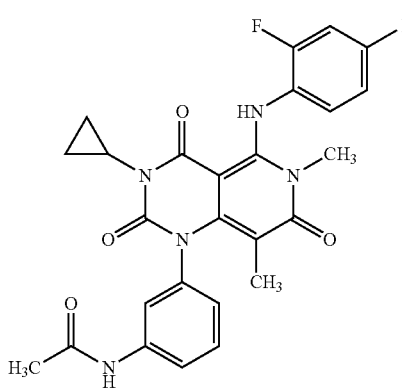

or a pharmaceutically acceptable salt or solvate thereof; and wherein the mammal has been diagnosed with advanced melanoma that tests positive for a BRAF V600 mutation.

2. The method of claim 1, wherein the mammal is a human, the Compound B is N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof and the Compound A is N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate thereof.

3. The method of claim 1, wherein the mammal is a human, the Compound B is N-{3-[5-(2-Amino-4-pyrimidinyl)-2-(1,1-dimethylethyl)-1,3-thiazol-4-yl]-2-fluorophenyl}-2,6-difluorobenzenesulfonamide methanesulfonate, and the Compound A is N-13-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide dimethyl sulfoxide solvate.

4. The method of claim 1, wherein the combination therapy comprises trametinib, dabrafenib and the anti-human PD-1 antibody.

5. The method of claim 4, wherein the therapeutically effective amount of the anti-human PD-1 antibody is 2 mg/kg once every 3 weeks or 10 mg/kg once every 2 weeks, the therapeutically effective amount of trametinib is 2 mg once daily and the therapeutically effective amount of dabrafenib is 150 mg twice daily.

6. A method of treating melanoma in a mammal comprising administering to said mammal a combination therapy, wherein the combination therapy comprises a therapeutically effective amount of an anti-human PD-1 antibody and a therapeutically effective amount of a Compound A, wherein:

the anti-human PD-1 antibody comprises a heavy chain comprising the sequence of amino acids set forth in SEQ ID NO: 21 and a light chain comprising the sequence of amino acids set forth in SEQ ID NO: 22; the Compound A is a compound of structure (I):

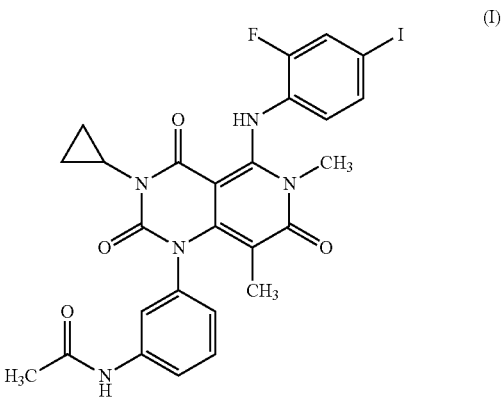 [SMILES: CC(=O)Nc1cccc(-n2c(=O)n(C3CC3)c(=O)c3c(Nc4ccc(I)cc4F)n(C)c(=O)c(C)c32)c1]

or a pharmaceutically acceptable salt or solvate thereof; and wherein the human has been diagnosed with advanced melanoma that tests negative for a BRAF V600 mutation.

7. The method of claim 6, wherein the therapeutically effective amount of the anti-human PD-1 antibody is 2 mg/kg once every 3 weeks or 10 mg/kg once every 2 weeks and the therapeutically effective amount of trametinib is 2 mg once daily.

8. The method of claim 6, wherein the mammal is a human and the Compound A is N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate thereof.

9. The method of claim 6, wherein the mammal is a human and the Compound A is N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide dimethyl sulfoxide solvate.

10. The method of claim 6, wherein the combination therapy comprises trametinib and the anti-human PD-1 antibody.

* * * * *